United States Patent
Riley et al.

(10) Patent No.: US 9,457,024 B2
(45) Date of Patent: Oct. 4, 2016

(54) COMPOSITIONS, DOSAGE FORMS, AND CO-ADMINISTRATION OF AN OPIOID AGONIST COMPOUND AND A NON-STEROIDAL ANTI-INFLAMMATORY DRUG

(71) Applicant: Nektar Therapeutics, San Francisco, CA (US)

(72) Inventors: Timothy A. Riley, Alameda, CA (US); Juergen W. Pfeiffer, Moss Beach, CA (US); Hema Gursahani, Foster City, CA (US)

( * ) Notice: Subject to any disclaimer, the term of this patent is extended or adjusted under 35 U.S.C. 154(b) by 0 days.

(21) Appl. No.: 14/356,486

(22) PCT Filed: Nov. 6, 2012

(86) PCT No.: PCT/US2012/063725
§ 371 (c)(1),
(2) Date: May 6, 2014

(87) PCT Pub. No.: WO2013/070617
PCT Pub. Date: May 16, 2013

(65) Prior Publication Data
US 2014/0336214 A1   Nov. 13, 2014

Related U.S. Application Data

(60) Provisional application No. 61/556,693, filed on Nov. 7, 2011.

(51) Int. Cl.
| | | |
|---|---|---|
| A61K 31/44 | (2006.01) | |
| A61K 31/54 | (2006.01) | |
| A61K 31/40 | (2006.01) | |
| A61K 31/19 | (2006.01) | |
| A61K 31/485 | (2006.01) | |
| A61K 45/06 | (2006.01) | |
| A61K 31/75 | (2006.01) | |
| A61K 31/785 | (2006.01) | |
| A61K 31/196 | (2006.01) | |
| A61K 31/4468 | (2006.01) | |
| A61K 31/405 | (2006.01) | |
| A61K 31/192 | (2006.01) | |
| A61K 31/5415 | (2006.01) | |
| A61K 31/407 | (2006.01) | |

(52) U.S. Cl.
CPC ........... *A61K 31/485* (2013.01); *A61K 31/196* (2013.01); *A61K 31/4468* (2013.01); *A61K 31/75* (2013.01); *A61K 31/785* (2013.01); *A61K 45/06* (2013.01); *A61K 31/192* (2013.01); *A61K 31/405* (2013.01); *A61K 31/407* (2013.01); *A61K 31/5415* (2013.01)

(58) Field of Classification Search
CPC .......... A61K 31/5415; A61K 31/407; A61K 31/485; A61K 31/405; A61K 31/192; A61K 31/167; A61K 31/196
USPC ....................... 514/282, 629, 420, 570, 226.5
See application file for complete search history.

(56) References Cited

U.S. PATENT DOCUMENTS

| | | | |
|---|---|---|---|
| 2,628,962 | A | 2/1953 | Homeyer et al. |
| 2,649,454 | A | 8/1953 | Rapoport et al. |
| 2,654,756 | A | 10/1953 | Homeyer et al. |
| 2,806,033 | A | 9/1957 | Lewenstein et al. |
| 3,385,886 | A * | 5/1968 | Nicholson ............. C07C 29/147 514/916 |
| 5,672,662 | A | 9/1997 | Harris et al. |
| 2005/0136031 | A1 | 6/2005 | Bentley et al. |
| 2010/0048602 | A1 | 2/2010 | Riggs-Sauthier et al. |
| 2011/0021426 | A1 | 1/2011 | Toll et al. |
| 2011/0159048 | A1 | 6/2011 | Crain et al. |
| 2011/0237614 | A1 | 9/2011 | Jude-Fishburn et al. |
| 2012/0184581 | A1 | 7/2012 | Riggs-Sauthier et al. |
| 2013/0023553 | A1 | 1/2013 | Jude-Fishburn et al. |

FOREIGN PATENT DOCUMENTS

| | | |
|---|---|---|
| CN | 101410095 A | 4/2009 |
| EP | 2 022 778 | 2/2009 |
| WO | WO 02/098949 | 12/2002 |
| WO | WO 2007/103113 A2 | 9/2007 |
| WO | WO 2008/057579 | 5/2008 |
| WO | WO 2008/112288 | 9/2008 |
| WO | WO 2010/033195 | 3/2010 |
| WO | WO 2011/011543 | 1/2011 |
| WO | WO 2011/088140 | 7/2011 |

OTHER PUBLICATIONS

Adams, et al., "Development of a Self-Report Screening Instrument for Assessing Potential Opioid Medication Misuse in Chronic Pain Patients," Journal of Pain and Symptom Management, vol. 27, No. 5, pp. 440-459, (2004).

(Continued)

*Primary Examiner* — Kevin E Weddington

(57) ABSTRACT

The present invention relates generally to the co-administration of an opioid agonist compound and an analgesic compound. In addition, the invention relates to, among other things, dosage forms for co-administration of an opioid agonist compound and an analgesic compound, methods for administering an opioid agonist compound and an analgesic compound, compositions comprising an opioid agonist compound and an analgesic compound, dosage forms comprising an opioid agonist compound and an analgesic compound, and so on.

8 Claims, 2 Drawing Sheets

(56) References Cited

OTHER PUBLICATIONS

Atluri, et al., "Development of a Screening Tool to Detect the Risk of Inappropriate Prescription Opioid Use in Patients with Chronic Pain," Pain Physician, vol. 7, No. 3, pp. 333-338, (2004).
Chen, et al., "Synthesis and Properties of ABA Amphiphiles," J. Org. Chem., vol. 64, No. 18, pp. 6870-6873, (1999).
Ertl, et al., "Fast Calculation of Molecular Polar Surface Area as a Sum of Fragment-Based Contributions and Its Application to the Prediction of Drug Transport," J. Med. Chem., vol. 43, No. 20, pp. 3714-3717, (2000).
Kelder, et al., "Polar Molecular Surface as a Dominating Determinant for Oral Absorption and Brain Penetration of Drugs," Pharmaceutical Research, vol. 16, No. 10, pp. 1514-1519, (1999).
Manchikanti, et al., "Monitoring Opioid Adherence in Chronic Pain Patients: Tools, Techniques, and Utility," Pain Physician 2008; Opioids Special Issue, vol. 11, (pp. S155-S180).
Rubin, et al., "The Cell Biology of the Blood-Brain Barrier," Annu. Rev. Neurosci., vol. 22, pp. 11-28, (1999).
Summerfield, et al., "Central Nervous System Drug Disposition: The Relationship between in Situ Brain Permeability and Brain Free Fraction," The Journal of Pharmacology and Experimental Therapeutics, vol. 322, No. 1, pp. 205-213, (2007), and two page correction.
Tsuji, "Small Molecular Drug Transfer across the Blood-Brain Barrier via Carrier-Mediated Transport Systems," NeuroRx®: The Journal of the American Society for Experimental NeuroTherapeutics, vol. 2, No. 1, pp. 54-62, (2005).
Zelcer, et al., "Selective potentiation of opioid analgesia by nonsteroidal anti-inflammatory drugs," Brain Research, vol. 1040, pp. 151-156, (2005).
"WHO. The ICD-10 Classification of Mental and Behavioral Disorders: Clinical Descriptions and Diagnostic Guidelines." Geneva, Switzerland: WHO, 1992, pp. 1-267.
"WHO Expert Committee on Drug Dependence. $28^{th}$ Report." Geneva, Switzerland: WHO 1993, pp. 1-52.
PCT International Search Report and Written Opinion corresponding to PCT International Application No. PCT/US2012/063725 date of mailing Mar. 28, 2013.
PCT International Preliminary Report on Patentability corresponding to PCT International Application No. PCT/US2012/063725 date of mailing May 22, 2014.
Enzon Pharmaceuticals, Macromolecular Engineering Technologies, 16 pages, (2004).
NEKTAR™—Transforming Therapeutics, Nektar Molecule Engineering: Polyethylene Glycol and Derivatives for Advanced PEGylation, 24 pages, Catalog—2003, (Jul. 2003).
NEKTAR™—Transforming Therapeutics, Nektar Advanced PEGylation: Polyethylene Glycol and Derivatives for Advanced PEGylation, 27 pages, Catalog—2004, (Jul. 2004).
NEKTAR™—Transforming Therapeutics, Nektar Advanced PEGylation: Polyethylene Glycol and Derivatives for Advanced PEGylation, 33 pages, (Catalog 2005—2006).
NOF Corporation, PEG Derivatives, Phospholipid and Drug Delivery Materials for Pharmaceuticals, 46 pages, Catalogue 2003—$1^{st}$, (Jan. 2003).
NOF Corporation, PEG Derivatives, Phospholipid and Drug Delivery Materials for Pharmaceuticals, 27 pages, Catalogue 2003—$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; BIOTINS, 5 pages, (Apr. 2004).
Polypure Products, PEG amines; PEG acids and amino acids; PEG thiols and disulfides; BIOTINS, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
English Translation of Chinese Notification of the First Office Action in Chinese Patent Application No. 201280054543.0 date of notification Oct. 21, 2015.

\* cited by examiner

COMPOSITIONS, DOSAGE FORMS, AND CO-ADMINISTRATION OF AN OPIOID AGONIST COMPOUND AND A NON-STEROIDAL ANTI-INFLAMMATORY DRUG

CROSS REFERENCE TO RELATED APPLICATIONS

This application is a 35 U.S.C. §371 application of International Application No. PCT/US2012/063725, filed Nov. 6, 2012, designating the United States, which claims the benefit of priority under 35 U.S.C. §119(e) to U.S. Provisional Patent Application Serial No. 61/556,693, filed on Nov. 7, 2011, the disclosures of which are incorporated by reference in their entireties.

The present invention relates generally to the co-administration of an opioid agonist compound and an analgesic. In addition, the invention relates to, among other things, dosage forms for co-administration of an opioid agonist compound and an analgesic, methods for administering an opioid agonist compound and an analgesic, compositions comprising an opioid agonist compound and an analgesic, dosage forms comprising an opioid agonist compound and an analgesic, and so on.

Opioid agonists that target the mu opioid receptor are often administered in combination with a second analgesic, such as an antipyretic drug and/or a non-steroidal anti-inflammatory drug (NSAID). In some cases, it is believed that such combinations result in a additive, and in some cases, a synergistic effect when used for the treatment of pain. Examples of FDA approved combinations include PERCOCET® (oxycodone/acetaminophen) and VICODIN® (hydrocodone/acetaminophen). Due to the improved analgesic effect, such combinations may be dosed in a manner that lessens the amount of opioid administered to a patient ("opioid sparing"). Thus, the combinations provide a potential means for lessening the abuse potential of highly addictive opioids. Further, they may also lessen other side effects caused by opioids.

Even though measures have been taken to reduce the amount of opioids administered to patients, the abuse of opioids has risen to epidemic proportions in the United States. FDA Consumer Health Information, FDA Acts to Reduce Harm from Opioid Drugs, April 2011. The FDA estimates that in 2007, more than 33 million Americans misused opioids, an increase from 29 million five years earlier. While the U.S. government plans to address the epidemic through education and monitoring programs, such strategies may not sufficiently address the core of the problem, which is the addictive nature of the underlying opioid compounds.

One possible means to address the underlying addictive properties of opioids is to reduce the rate at which opioids enter the central nervous system. To this end, certain opioid agonist compounds have been prepared and are believed to reduce the rate of opioid entry into the central nervous system. U.S. Patent Application Publication No. 2010/0048602, International Patent Application Publication No. WO 2008/112288, International Patent Application Publication No. WO 2010/033195, U.S. Patent Application Publication No. 2011/0237614, International Patent Application Publication No. WO 2011/011543, U.S. Patent Application Publication No. 2012/0184581, International Patent Application Publication No. WO 2011/088140, and U.S. patent application Ser. No. 13/521,556. As a result, it is believed that the CNS side effects, including abuse potential, may be reduced by the administration of such opioid agonist compounds. While those compounds are believed to address some of the CNS side effects associate with opioids, the potential for peripheral side effects (e.g. constipation) may still exist. The combinations disclosed herein may be useful to address those side effects associated with opioids, as well as those associated with the analgesic compounds.

As such, there exists a need to further minimize the potential side effect profile of opioids and opioid agonist compounds. The present invention addresses this and other needs in the art.

In one or more embodiments of the present invention, a composition is provided, wherein the composition comprises an opioid agonist compound and at least one analgesic compound.

In one or more embodiments of the present invention, a composition is provided, wherein the composition comprises an opioid agonist compound chosen from the formula

OPIOID-X-POLY and pharmaceutically acceptable salts thereof; wherein OPIOID is a residue of an opioid agonist, X is a physiological stable linker, and POLY is a water soluble oligomer, and at least one analgesic compound.

In one or more embodiments of the present invention, a composition is provided, wherein the composition comprises an opioid agonist compound chosen from the formula OPIOID-X—$(CH_2CH_2O)_n$—Y and pharmaceutically acceptable salts thereof; wherein OPIOID is a residue of an opioid agonist, X is a physiologically stable linker, n is an integer from 1 to 10, and Y is selected from hydrogen, an end capping group, and a protecting group; and at least one analgesic compound.

In one or more embodiments of the present invention, a unit dosage form of a composition is provided, wherein the composition comprises an opioid agonist compound; and at least one analgesic compound.

In one or more embodiments of the present invention, a unit dosage form of a composition is provided, wherein the composition comprises an opioid agonist compound chosen from the formula

OPIOID-X-POLY and pharmaceutically acceptable salts thereof; wherein OPIOID is a residue of an opioid agonist, X is a physiologically stable linker, n is an integer from 1 to 10; and at least one analgesic compound.

In one or more embodiments of the present invention, a method of treating pain is provided, wherein the method comprises administering a composition, wherein the composition comprises an opioid agonist compound and at least one analgesic compound.

In one or more embodiments of the present invention, a method of treating pain is provided, wherein the method comprises administering a composition, wherein the composition comprises an opioid agonist compound chosen from the formula

OPIOID-X-POLY and pharmaceutically acceptable salts thereof; wherein OPIOID is a residue of an opioid agonist, X is a physiological stable linker, and POLY is a water soluble oligomer, and at least one analgesic compound.

In one or more embodiments of the present invention, a method of treating pain is provided, wherein the method comprises administering a unit dosage form of a composition, wherein the composition comprises an opioid agonist compound; and at least one analgesic compound.

In one or more embodiments of the present invention, a method of treating pain is provided, wherein the method comprises administering a unit dosage form of a composition, wherein the composition comprises an opioid agonist compound chosen from the formula

OPIOID-X-POLY and pharmaceutically acceptable salts thereof; wherein OPIOID is a residue of an opioid agonist, X is a physiological stable linker, and POLY is a water soluble oligomer, and at least one analgesic compound.

In one or more embodiments of the present invention, a method of treating pain is provided, wherein the method comprises administering an opioid agonist compound and at least one analgesic compound.

In one or more embodiments of the present invention, a method of treating pain is provided, wherein the method comprises administering an opioid agonist compound chosen from the formula

OPIOID-X-POLY and pharmaceutically acceptable salts thereof; wherein OPIOID is a residue of an opioid agonist, X is a physiological stable linker, and POLY is a water soluble oligomer, and at least one analgesic compound.

These and other objects, aspects, embodiments, and features of the invention will become more fully apparent when read in conjunction with the detailed description of the invention.

Figure 1:
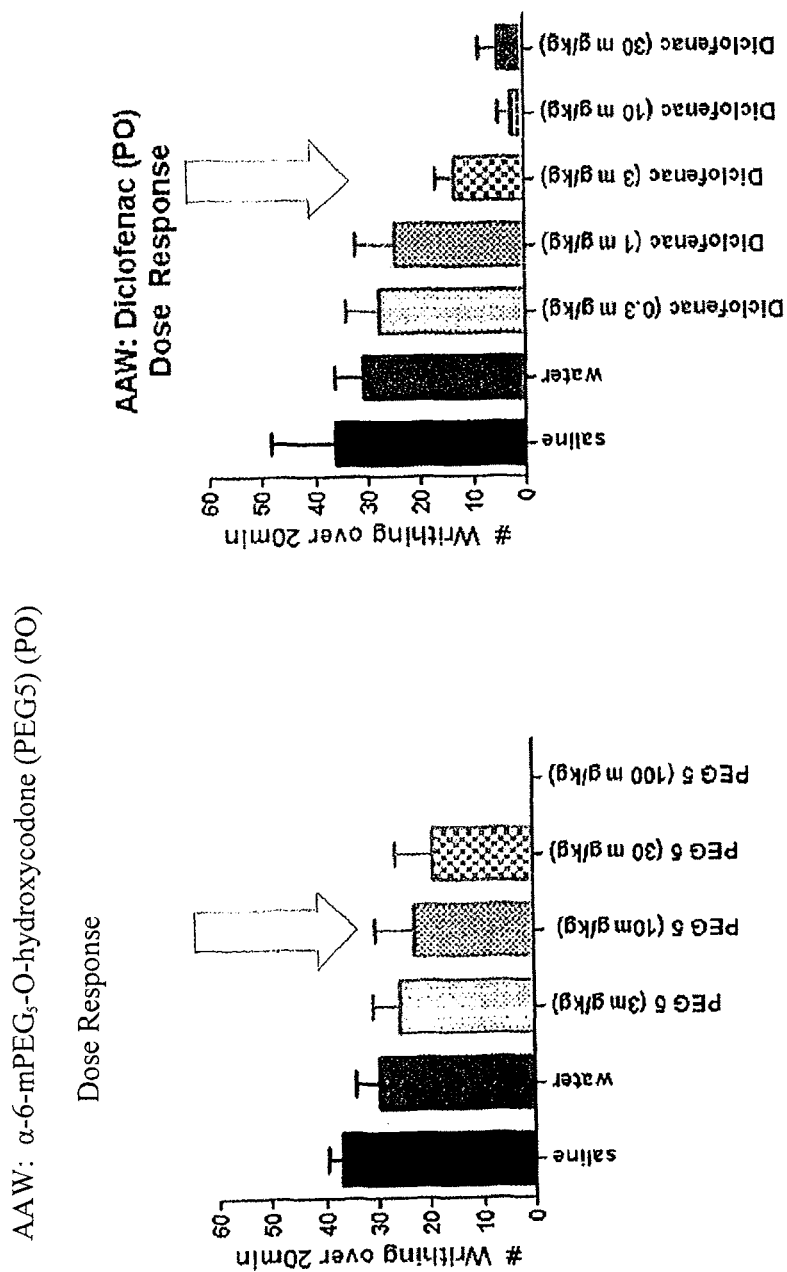
FIG. 1 depicts the dose response curves for certain opioid agonist compounds and analgesics as described in Example 7.

In describing and claiming the present invention, the following terminology will be used in accordance with the definitions described below.

The terms "opioid drug" and "opioid agonist" are broadly used herein to refer to an organic, inorganic, or organometallic compound typically having a molecular weight of less than about 1000 Daltons (and typically less than 500 Daltons) and having some degree of activity as a mu, delta and/or kappa agonist. Opioid agonists encompass oligopeptides and other biomolecules having a molecular weight of less than about 1500.

The term "opioid agonist compound" as used herein, refers to an opioid agonist (or residue thereof) bound to a water soluble oligomer through a linker, including pharmaceutically acceptable salts thereof. In certain embodiments, the opioid agonist compound has the formula OPIOID-X-POLY. Further embodiments of opioid agonist compounds are disclosed herein.

The terms "spacer moiety," "linkage" and "linker" are used herein interchangeably to refer to an atom or a collection of atoms optionally used to link interconnecting moieties such as a terminus of a polymer segment and an opioid drug or an electrophile or nucleophile of an opioid drug. The linker moiety may be hydrolytically stable or may include a physiologically hydrolyzable or enzymatically degradable linkage. Unless the context clearly dictates otherwise, a linker moiety optionally exists between any two elements of an opioid agonist compound (e.g., the provided opioid agonist compounds comprising a residue of an opioid agonist and a water-soluble oligomer that can be attached directly or indirectly through a linker moiety).

"Water soluble oligomer" indicates a non-peptidic oligomer that is at least 35% (by weight) soluble, in certain embodiments greater than 70% (by weight), and in certain embodiments greater than 95% (by weight) soluble, in water at room temperature. Typically, an unfiltered aqueous preparation of a "water-soluble" oligomer transmits at least 75%, and in certain embodiments at least 95%, of the amount of light transmitted by the same solution after filtering. In certain embodiments the water-soluble oligomer is at least 95% (by weight) soluble in water or completely soluble in water. With respect to being "non-peptidic," an oligomer is non-peptidic when it has less than 35% (by weight) of amino acid residues.

As described herein, the opioid agonist compounds include not only the opioid agonist compounds themselves, but also the pharmaceutically acceptable salts or salt forms of the opioid agonist compound as well. An opioid agonist compound as described herein can possess a sufficiently acidic group, a sufficiently basic group, or both functional groups, and, accordingly, react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xyienesuifonate, phenylacetate, phenylpropionate, phenyibutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. In certain embodiments oligomers used in connection with the present invention are homo-oligomers. The water-soluble oligomer typically comprises one or more monomers serially attached to form a chain of monomers. The oligomer can be formed from a single monomer type (i.e., is homo-oligomeric) or two or three monomer types (i.e., is co-oligomeric).

As used herein, the structure  represents a bond, which may be selected from a single bond or a double bond.

That is the solid line represents a bond and the dashed line represents an optional bond. When the optional bond is absent, the result is a single bond. When the optional bond is present, the result is a double bond.

An "oligomer" is a molecule possessing from about 2 to about 50 monomers, in certain embodiments from about 2 to about 30 monomers. The architecture of an oligomer can vary. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" (also called an oligoethylene glycol) is one in which substantially all (and in certain embodiments all) monomeric subunits are ethylene oxide subunits. The oligomer may, however, contain distinct end capping moieties or functional groups, e.g., for conjugation. Typically, PEG oligomers for use in the present invention will comprise one of the two following structures: "—$(CH_2CH_2O)_n$—" or "—$(CH_2CH_2O)_{n-1}CH_2CH_2$—," depending upon whether the terminal oxygen(s) has been displaced, e.g., during a synthetic transformation. For PEG oligomers, "n" varies from about 2 to 50, in certain embodiments from about 2 to about 30, and the terminal groups and architecture of the overall PEG can vary. When PEG further comprises a functional group, A, for linking to, e.g., an opioid agonist, the functional group when covalently attached to a PEG oligomer does not result in formation of (i) an oxygen-oxygen bond (—O—O—, a peroxide linkage), or (ii) a nitrogen-oxygen bond (N—O, O—N).

An "end capping group" is generally a non-reactive carbon-containing group attached to a terminal oxygen of a PEG oligomer. Exemplary end capping groups comprise a $C_{1-5}$ alkyl group, such as methyl, ethyl and benzyl), as well as aryl, heteroaryl, cyclo, heterocyclo, and the like. In certain embodiments the capping groups have relatively low molecular weights such as methyl or ethyl. The end-capping group can also comprise a detectable label. Such labels include, without limitation, fluorescers, chemiluminescers, moieties used in enzyme labeling, colorimetric labels (e.g., dyes), metal ions, and radioactive moieties.

"Branched", in reference to the geometry or overall structure of an oligomer, refers to an oligomer having two or more polymers representing distinct "arms" that extend from a branch point.

"Forked" in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, Protecting Groups in Organic Synthesis, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" bond is a hydrolyzable bond or an enzymatically degradable linkage. A "hydrolyzable" or "degradable" bond is a relatively labile bond that reacts with water (i.e., is hydrolyzed) under ordinary physiological conditions. The tendency of a bond to hydrolyze in water under ordinary physiological conditions will depend not only on the general type of linkage connecting two central atoms but also on the substituents attached to these central atoms. Such bonds are generally recognizable by those of ordinary skill in the art. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes under ordinary physiological conditions.

"Releasably attached," e.g., in reference to an opioid drug releasably attached to a water-soluble oligomer, refers to an opioid drug that is covalently attached via a linker that includes a physiologically cleavable or degradable (including enzymatically) linkage as disclosed herein, wherein upon degradation (e.g., by hydrolysis), the opioid drug is released. The opioid drug thus released will typically correspond to the unmodified opioid agonist, or may be slightly altered, e.g., possessing a short organic tag of about 8 atoms, e.g., typically resulting from cleavage of a part of the water-soluble oligomer linker not immediately adjacent to the opioid agonist compound. In certain embodiments, the unmodified opioid drug is released.

A "stable" linkage or bond refers to a chemical moiety or bond, typically a covalent bond, that is substantially stable in water, that is to say, does not undergo hydrolysis under ordinary physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under ordinary physiological conditions. Hydrolysis rates of representative chemical bonds can be found in most standard chemistry textbooks.

In the context of describing the consistency of oligomers in a given composition, "substantially" or "essentially" means nearly totally or completely, for instance, 95% or greater, in certain embodiments 97% or greater, in certain embodiments 98% or greater, in certain embodiments 99% or greater, and in certain embodiments 99.9% or greater.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially comprising molecules having a single and definable number of monomers rather than several different numbers of monomers (i.e., an oligomer composition having three or more different oligomer sizes). In certain embodiments, a monodisperse oligomer composition possesses a MW/Mn value of 1.0005 or less, and in certain embodiments, a MW/Mn value of 1.0000. By extension, a composition comprised of monodisperse opioid agonist compounds means that substantially all oligomers of all opioid agonist compounds in the composition have a single and definable number (as a whole number) of monomers rather than a distribution and would possess a MW/Mn value of 1.0005, and in certain embodiments, a MW/Mn value of 1.0000 if the oligomer were not attached to the residue of the opioid agonist. A composition comprised of monodisperse opioid agonist compounds can include, however, one or more additional substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a distribution, and whose distribution of molecular weights, when plotted as a number fraction versus molecular weight, appears as two separate identifiable peaks. In certain embodiments, for a bimodal oligomer composition as described herein, each peak is generally symmetric about its mean, although the size of the two peaks may differ. Ideally, the polydispersity index of each peak in the bimodal distribution, Mw/Mn, is 1.01 or less, in certain embodiments 1.001 or less, in certain embodiments 1.0005 or less, and in certain embodiments a MW/Mn value of 1.0000. By extension, a composition comprised of bimodal opioid agonist compounds means that substantially all oligomers of all opioid agonist compounds in the composition have one of two definable and different numbers (as whole numbers) of monomers rather than a large distribution and would possess a MW/Mn value of 1.01 or less, in certain embodiments 1.001 or less, in certain embodiments 1.0005 or less, and in certain embodiments a MW/Mn value of 1.0000 if the oligomer were not attached to the residue of the opioid agonist. A composition comprised of bimodal opioid agonist compounds can include, however, one or more additional substances such as solvents, reagents, excipients, and so forth.

A "biological membrane" is any membrane, typically made from specialized cells or tissues, that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, rectal mucosa, and so forth. In certain contexts the term "biological membrane" does not include those membranes associated with the middle gastro-intestinal tract (e.g., stomach and small intestines). For example, in some instances it may be desirable for an opioid agonist compound of the invention to have a limited ability to cross the blood-brain barrier, yet be desirable that the same compound cross the middle gastro-intestinal tract.

A "biological membrane crossing rate," as used herein, provides a measure of a compound's ability to cross a biological membrane (such as the membrane associated with the blood-brain barrier). A variety of methods can be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known in the art, described herein and/or in the relevant literature, and/or can be determined by one of ordinary skill in the art.

"Alkyl" refers to a hydrocarbon chain, typically ranging from about 1 to 20 atoms in length. Such hydrocarbon chains are preferably but not necessarily saturated and may be branched or straight chain. In certain embodiments the hydrocarbon chain is a straight chain. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced. In certain embodiments, alkyl includes both a straight chain and a cyclic alkyl portion, such as cyclobutylmethyl, cyclopropylmethyl, and the like. An "alkenyl" group is an alkyl of 2 to 20 carbon atoms with at least one carbon-carbon double bond.

The terms "substituted alkyl" or "substituted $C_{q\text{-}r}$ alkyl" where q and r are integers identifying the range of carbon atoms contained in the alkyl group, denotes the above alkyl groups that are substituted by one, two or three halo (e.g., F, Cl, Br, I), trifluoromethyl, hydroxy, $C_{1-7}$ alkyl (e.g., methyl, ethyl, n-propyl, isopropyl, butyl, t-butyl, and so forth), $C_{1-7}$ alkoxy, $C_{1-7}$ acyloxy, $C_{3-7}$ heterocyclic, amino, phenoxy, nitro, carboxy, carboxy, acyl, cyano. The substituted alkyl groups may be substituted once, twice or three times with the same or with different substituents.

"Lower alkyl" refers to an alkyl group containing from 1 to 6 carbon atoms, and may be straight chain or branched, as exemplified by methyl, ethyl, n-butyl, i-butyl, t-butyl. "Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, in certain embodiments $C_1$-$C_{20}$ alkyl (e.g., methoxy, ethoxy, propyloxy, benzyl, etc.), and in certain embodiments $C_1$-$C_7$.

"Acyl" refers to a —C(O)R group, wherein R is an organic radical. In certain embodiments R may be selected from alkyl, substituted alkyl, aryl, and substituted aryl.

"Pharmaceutically acceptable excipient" or "pharmaceutically acceptable carrier" refers to component that can be included in the compositions of the invention in order to provide for a composition that has an advantage (e.g., more suited for administration to a patient) over a composition lacking the component and that is recognized as not causing significant adverse toxicological effects to a patient.

The term "aryl" means an aromatic group having up to 14 carbon atoms. Aryl groups include phenyl, naphthyl, biphenyl, phenanthrenyl, naphthacenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, hydroxy, cyano, nitro, alkyl (e.g., $C_{1-6}$ alkyl), alkoxy (e.g., $C_{1-6}$ alkoxy), benzyloxy, carboxy, aryl, and so forth.

An "aromatic-containing moiety" is a collection of atoms containing at least aryl and optionally one or more atoms. Suitable aromatic-containing moieties are described herein.

"Pharmacologically effective amount," "physiologically effective amount," and "therapeutically effective amount" are used interchangeably herein to mean the amount of opioid agonist compound and/or analgesic present in a composition that is needed to provide a threshold level of opioid agonist compound and/or analgesic in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterobifunctional.

A basic reactant or an acidic reactant described herein include neutral, charged, and any corresponding salt forms thereof.

The term "patient," refers to a living organism suffering from or prone to a condition that can be prevented or treated by administration of a composition as described herein, typically, but not necessarily, in the form of a composition comprising an opioid agonist compound and an analgesic, and includes both humans and animals.

"Optional" or "optionally" means that the subsequently described circumstance may but need not necessarily occur, so that the description includes instances where the circumstance occurs and instances where it does not.

Unless the context clearly dictates otherwise, when the term "about" precedes a numerical value, the numerical value is understood to mean the stated numerical value and also ±10% of the stated numerical value.

In certain embodiments, a composition comprising an opioid agonist compound; and an analgesic compound is provided.

In certain embodiments, a composition comprising an opioid agonist compound chosen from the formula

OPIOID-X-POLY and pharmaceutically acceptable salts thereof, wherein OPIOID is a residue of an opioid agonist, X is a physiological stable linker, and POLY is a water soluble oligomer; and an analgesic compound, is provided.

In certain embodiments, a composition comprising an opioid agonist compound chosen from the formula OPIOID-X—(CH$_2$CH$_2$O)$_n$—Y and pharmaceutically acceptable salts thereof, wherein OPIOID is a residue of an opioid agonist, X is a physiologically stable linker, n is an integer from 2 to 10, and Y is selected from hydrogen, an end capping group, and a protecting group; and an analgesic compound, is provided.

In certain embodiments, the opioid agonist compound is chosen from the structure

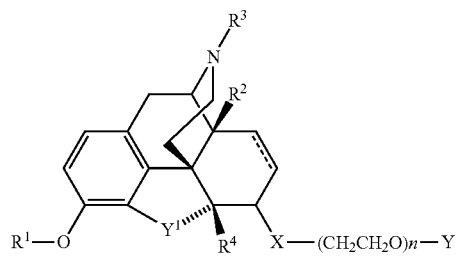

wherein:
$R^1$ is selected from hydrogen, acyl, and lower alkyl;
$R^2$ is selected from hydrogen and hydroxyl;
$R^3$ is selected from hydrogen and alkyl;
$R^4$ is hydrogen;
"———" represents an optional bond;
$Y^1$ is selected from O and S;
X is a physiologically stable linkage;
n is an integer from 2 to 10; and
Y is an end capping group; and pharmaceutically acceptable salts thereof In certain embodiments, $R^1$ is selected from hydrogen and methyl; $R^3$ is selected from hydrogen, methyl, and cyclobutylmethyl; $R^4$ is hydrogen; $Y^1$ is O; n is an integer from 2 to 10; and Y is lower alkyl.

In certain embodiments, Y is a capping group. In certain embodiments, Y is an alkyl group. In certain embodiments, Y is a lower alkyl group. In certain embodiments, Y is methyl.

In certain embodiments, the opioid agonist compound is chosen from

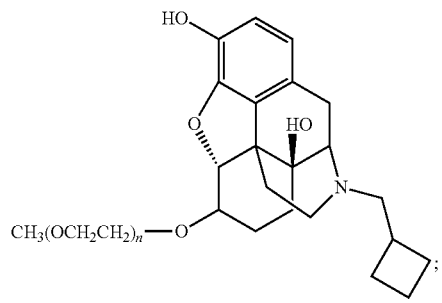

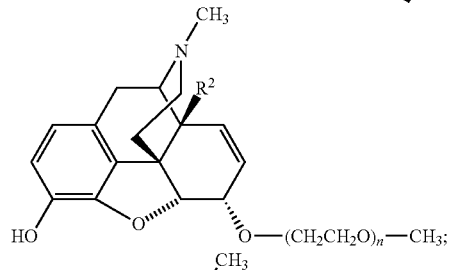

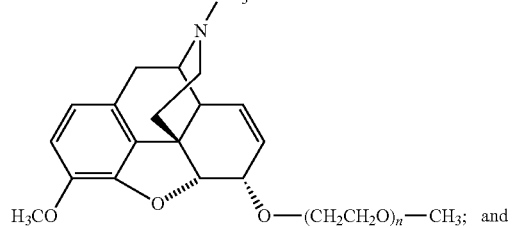

-continued

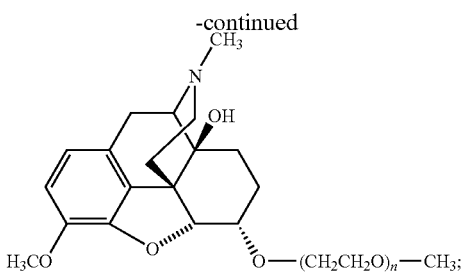

wherein n is an integer selected from 2 to 10; and pharmaceutically acceptable salts thereof In certain embodiments, the opioid agonist compound is chosen from the structure:

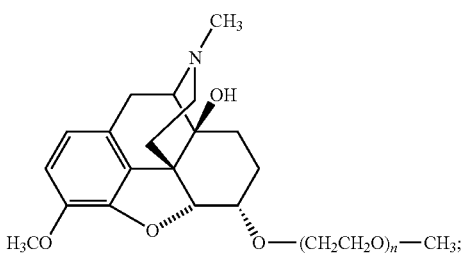

wherein n is an integer selected from 2 to 10; and pharmaceutically acceptable salts thereof.

In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8. In certain embodiments, n is 9. In certain embodiments, n is 10.

In certain embodiments, the opioid agonist compound has a structure chosen from

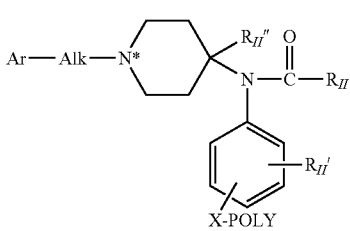

Formula II-Ca wherein:

N* is nitrogen;

Ar is selected from the group consisting of cyclohexyl, phenyl, halophenyl, methoxyphenyl, aminophenyl, pyridyl, furyl and thienyl;

Alk is selected from the group consisting of ethylene and propylene;

$R_{II}$ is selected from the group consisting of lower alkyl, lower alkoxy, dimethylamino, cyclopropyl, 1-pyrrolidyl, morpholino;

$R_{II}'$ is selected from the group consisting of hydrogen, methyl and methoxy;

$R_{II}''$ is hydrogen;

X is a linker (e.g., a covalent bond "—" or one or more atoms); and

POLY is a water-soluble, non-peptidic oligomer; and pharmaceutically acceptable salts thereof.

In certain embodiments of a compound of Formula II-Ca, $R_{II}$ is lower alkyl. In certain embodiments of a compound of Formula II-Ca, $R_{II}$ is ethyl. In certain embodiments of a compound of Formula II-Ca, Ar is phenyl. In certain embodiments of a compound of Formula II-Ca, Alk is ethylene. In certain embodiments of a compound of Formula II-Ca, $R_{II}'$ is hydrogen. In certain embodiments of a compound of Formula II-Ca, POLY is an alkylene glycol oligomer. In certain embodiments of a compound of Formula II-Ca, POLY is an ethylene glycol oligomer.

With respect to Formula II-Ca, it will be understood that, depending on the conditions, one or both of the amines—but more typically, the amine marked with an asterisk ("N*") in Formula II-Ca—can be protonated.

In certain embodiments, the opioid agonist compound has a structure chosen from

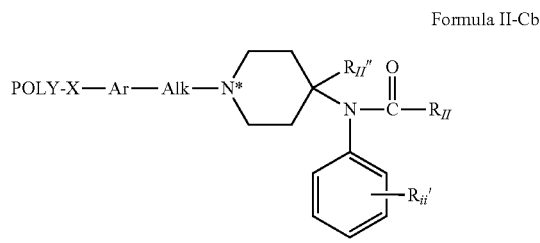

Formula II-Cb wherein:

N* is nitrogen;

Ar is selected from the group consisting of cyclohexyl, phenyl, halophenyl, methoxyphenyl, aminophenyl, pyridyl, furyl and thienyl;

Alk is selected from the group consisting of ethylene and propylene;

$R_{II}$ is selected from the group consisting of lower alkyl, lower alkoxy, dimethylamino, cyclopropyl, 1-pyrrolidyl, morpholino;

$R_{II}'$ is selected from the group consisting of hydrogen, methyl and methoxy;

$R_{II}''$ is hydrogen;

X is a linker (e.g., a covalent bond "—" or one or more atoms); and

POLY is a water-soluble, non-peptidic oligomer; and pharmaceutically acceptable salts thereof.

In certain embodiments of a compound of Formula II-Cb, $R_{II}$ is lower alkyl. In certain embodiments of a compound of Formula II-Cb, $R_{II}$ is ethyl. In certain embodiments of a compound of Formula II-Cb, Ar is phenyl. In certain embodiments of a compound of Formula II-Cb, Alk is ethylene. In certain embodiments of a compound of Formula II-Cb, $R_{II}'$ is hydrogen. In certain embodiments of a compound of Formula II-Cb, POLY is an alkylene glycol oligomer. In certain embodiments of a compound of Formula II-Cb, POLY is an ethylene glycol oligomer.

With respect to Formula II-Cb, it will be understood that, depending on the conditions, one or both of the amines—but more typically, the amine marked with an asterisk ("N*") in Formula II-Cb—can be protonated.

In certain embodiments, the opioid agonist compound has a structure chosen from

Formula II-Cc

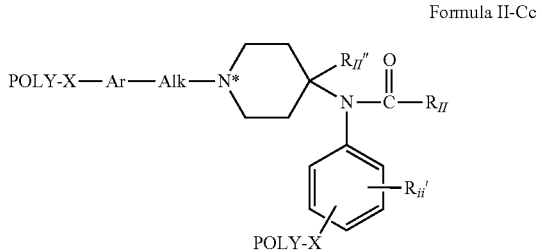

embodiments of a compound of Formula II-Cc, Alk is ethylene. In certain embodiments of a compound of Formula II-Cc, $R_{II}'$ is hydrogen. In certain embodiments of a compound of Formula II-Cc, POLY is an alkylene glycol oligomer. In certain embodiments of a compound of Formula II-Cc, POLY is an ethylene glycol oligomer.

With respect to Formula II-Cc, it will be understood that, depending on the conditions, one or both of the amines—but more typically, the amine marked with an asterisk ("N*") in Formula II-Cc—can be protonated.

In certain embodiments the opioid agonist compound has a structure chosen from:

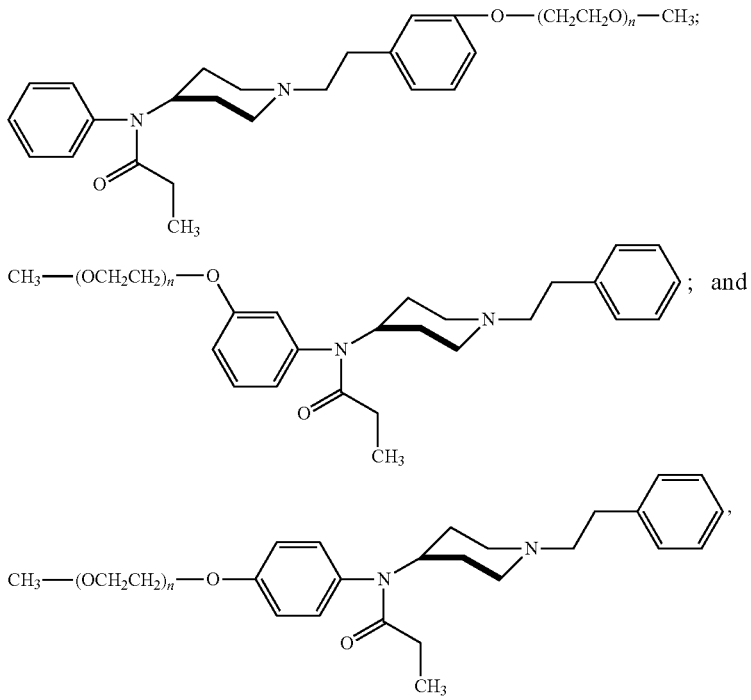

wherein:

N* is nitrogen;

Ar is selected from the group consisting of cyclohexyl, phenyl, halophenyl, methoxyphenyl, aminophenyl, pyridyl, furyl and thienyl;

Alk is selected from the group consisting of ethylene and propylene;

$R_{II}$ is selected from the group consisting of lower alkyl, lower alkoxy, dimethylamino, cyclopropyl, 1-pyrrolidyl, morpholino;

$R_{II}'$ is selected from the group consisting of hydrogen, methyl and methoxy;

$R_{II}''$ is hydrogen;

each X is independently a linker (e.g., a covalent bond "—" or one or more atoms); and each POLY is independently a water-soluble, non-peptidic oligomer; and pharmaceutically acceptable salts thereof.

In certain embodiments of a compound of Formula II-Cc, $R_{II}$ is lower alkyl. In certain embodiments of a compound of Formula II-Cc, $R_{II}$ is ethyl. In certain embodiments of a compound of Formula II-Cc, Ar is phenyl. In certain wherein "n" is an integer from 1 to 30; and pharmaceutically acceptable salts thereof. In certain embodiments, "n" is an integer from 1 to 10. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8. In certain embodiments, n is 9. In certain embodiments, n is 10.

In certain embodiments, the analgesic compound is a non-steroidal anti-inflammatory drug (NSAID). In certain embodiments, the analgesic compound is an antipyretic. In certain embodiments, a single analgesic compound is present in the composition.

In certain embodiments, the analgesic compound is selected from ketorolac, ibuprofen, oxaprozin, indomethecin, etodolac, meloxicam, sulindac, diclofenac, flufenamic acid, difunisal, naproxen, flurbiprofen, ketoprofen, fenoprofen, and acetaminophen.

In certain embodiments, the composition is in a unit dosage form.

In certain embodiments, the compositions disclosed herein are understood to be suitable for pharmaceutical administration. In certain embodiments, the compositions are pharmaceutical compositions.

As indicated above, the present disclosure is directed to (among other things) a composition (or combination) comprising opioid agonist compounds chosen from the formula:

OPIOID-X-POLY and pharmaceutically acceptable salts thereof, wherein OPIOID is a residue of an opioid agonist, X is a physiological stable linker, and POLY is a water soluble oligomer, and an analgesic compound. While both the opioid agonist compounds and analgesic are understood to alleviate pain when administered individually, the present combinations provide an additive effect when administered for the treatment of pain. In certain embodiments, a synergistic effect may be observed when administered for the treatment of pain. That is, the analgesic effect of the combination is larger than the sum of the analgesic effect of each individual component when administered alone.

The ability of the compositions and combinations disclosed herein to treat pain may be measured by assays known to one of skill in the art. Certain assays may include, but are not limited to, acid writhing assays (e.g. acetic acid, phenylquinone), carageenan assay, complete Freund's adjuvant assay, formalin paw assay, and the radiant heat tail-flick assay. The compositions and combinations disclosed herein may be tested in a suitable analgesic assay. In certain embodiments, several dosages of each opioid agonist compound and analgesic will be administered individually and measured using an appropriate assay for measuring an analgesic effect. Based on the results of the individual administration, a suitable dose of each component (opioid agonist compound and analgesic) may be tested in combination.

While it is known in the art that certain combinations of opioids and analgesics provide an additive and possibly synergistic effect, the literature indicates that such effects may be difficult to predict. Zelcer et al., *Brain Research*, 1040 (2005), pp. 151-156. Factors that may be relevant to the combined effect are reportedly the analgesic administered, the opioid administered, the type of pain and/or the particular pain model employed when measuring the effect of the administration of such combinations.

It is believed that the combinations and compositions disclosed herein will have several therapeutic advantages. The combination may allow for reduced dosing and therefore reduced side effects from either of the components (opioid agonist compound and analgesic compound), thus improving the overall therapeutic window for the combination. Such a combination may also increase the suitability of the composition/combination for chronic use.

The compositions described herein may also comprise one or more pharmaceutical excipients. Exemplary excipients include, without limitation, carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the opioid agonist compound or other components of the preparation (e.g. analgesic). Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the opioid agonist compound and the analgesic in the composition will vary depending on a number of factors, but will optimally be a therapeutically effective dose when the composition is stored in a unit dose container. A therapeutically effective dose can be determined experimentally by repeated administration of increasing amounts of the active components in order to determine which amounts produce a clinically desired endpoint. Generally, a therapeutically effective amount of each component (e.g. opioid agonist compound and/or analgesic) will range from about 0.001 mg to 1000 mg, in certain embodiments from about 0.01 mg to about 750 mg, and in certain embodiments from about 0.10 mg to about 500 mg.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, in certain embodiments from about 5%-98% by weight, in certain embodiments from about 15-95% by weight of the excipient, and in certain embodiments concentrations less than 30% by weight.

These foregoing pharmaceutical excipients along with other excipients and general teachings regarding pharmaceutical compositions are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical compositions can take any number of forms and the invention is not limited in this regard. In certain embodiments, preparations are in a form suitable for oral administration such as a tablet, caplet, capsule, gel cap, troche, dispersion, suspension, solution, elixir, syrup, lozenge, but can be in other forms as well, such as transdermal patch, spray, suppository, and powder.

Oral dosage forms are preferred and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the compositions described herein. In addition to the active components, the tablets and caplets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

In certain embodiments, the oral dosage form is a capsule, in which the composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The composition can also be administered through the skin using conventional transdermal patch or other transdermal delivery system, wherein the composition is contained within a laminated structure that serves as a drug delivery device to be affixed to the skin. In such a structure, the opioid agonist compound and/or analgesic is contained in a layer, or "reservoir," underlying an upper backing layer. The laminated structure can contain a single reservoir, or it can contain multiple reservoirs.

The composition can also be formulated into a suppository for rectal administration. With respect to suppositories, the opioid agonist compound and analgesic are mixed with a suppository base material which is (e.g., an excipient that remains solid at room temperature but softens, melts or dissolves at body temperature) such as cocoa butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the opioid agonist compound and/or analgesic (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering the composition as provided herein to a patient suffering from a condition that is responsive to treatment with the opioid agonist compound and/or analgesic, such as pain. The method comprises administering, generally orally, a therapeutically effective amount of the composition. The method specifically includes compositions comprising combinations of any of the opioid agonist compounds disclosed herein and any of the analgesic compounds disclosed herein. Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

The invention also provides a method for administering an opioid agonist compound and at least one analgesic compound, as provided herein, to a patient suffering from a condition that is responsive to treatment with the opioid agonist compound and/or analgesic, such as pain. The method specifically includes combinations of any of the opioid agonist compounds disclosed herein and any of the analgesic compounds disclosed herein. In such a method, in certain embodiments, the opioid agonist compound and at least one analgesic compound are not administered as part of the same composition. The method comprises administering, generally orally, a therapeutically effective amount of an opioid agonist compound and at least one analgesic compound. Each may be present in a separate composition, and in certain embodiments, each separate composition is present in a separate unit dosage form. Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously (e.g., polymers), with molecular weights ranging from about 500 to 30 kilodaltons (e.g., having molecular weights of about 500 daltons, 1000 daltons, 2000 daltons, 2500 daltons, 3000 daltons, 5000 daltons, 7500 daltons, 10000 daltons, 15000 daltons, 20000 daltons, 25000 daltons, 30000 daltons or even more).

The methods of administering may be used to treat any condition that can be remedied or prevented by administration of the particular opioid agonist compound and analgesic. Most commonly, the compositions and combinations provided herein are administered for the management of chronic pain. As such, the methods disclosed herein include methods for treating pain, for example, by administering the compositions and combinations provided herein. Those of ordinary skill in the art appreciate which conditions a specific opioid agonist compound and analgesic can effectively treat. The actual dose to be administered will vary depend upon the age, weight, and general condition of the subject as well as the severity of the condition being treated, the judgment of the health care professional, opioid agonist compound, and analgesic being administered. Therapeutically effective amounts are known to those skilled in the art and/or are described in the pertinent reference texts and literature. Generally, a therapeutically effective amount of each component (e.g. opioid agonist compound and/or analgesic) will range from about 0.001 mg to 1000 mg, in certain embodiments in doses from 0.01 mg to 750 mg, and in certain embodiments in doses from 0.10 mg to 500 mg.

In certain embodiments, the composition will be in a unit dosage form to thereby provide a unit dosage suitable for single administration of a dosage of each active component in the unit dosage form. Suitable pharmaceutical compositions and dosage forms may be prepared using conventional methods known to those in the field of pharmaceutical formulation and described in the pertinent texts and literature, e.g., in Remington's Pharmaceutical Sciences: 18$^{th}$ Edition, Gennaro, A. R., Ed. (Mack Publishing Company; Easton, Pa.; 1990).

The unit dosage of the composition can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

Based on the covalent modification of opioid agonist molecules, the opioid agonist compounds present in the disclosed compositions and combinations represent an improvement over the opioid agonist formulations of the prior art. That is to say, opioid agonist compounds containing small water-oligomers possess altered pharmacokinetic profiles, but are not subject to the risk of physical tampering that allows for the recovery and abuse of the rapid acting opioid agonists associated with certain alternative delivery formulations such as transdermal patches. U.S. Patent Application Publication No. 2010/0048602, International Patent Application Publication No. WO 2008/112288, International Patent Application Publication No. WO 2010/033195, U.S. Patent Application Publication No. 2011/0237614, International Patent Application Publication No. WO 2011/011543, U.S. Patent Application Publication No. 2012/0184581, International Patent Application Publication No. WO 2011/088140, and U.S. patent application Ser. No. 13/521,556. The opioid agonist compounds themselves may be useful for eliminating the euphoric high associated with administration of opioids while still maintaining an analgesic effect comparable to that of unmodified opioid. The opioid agonist compounds are also useful in reducing or eliminating CNS-side effects associated with opioid use, as well as in reducing the associated addiction and/or abuse potential associated therewith. As such, these and other beneficial properties will also be present in the compositions and combinations of the present invention.

Accordingly, OPIOID can be any opioid agonist, including any compound interacting with mu (μ), kappa (κ), or delta (δ) opioid receptors, or any combination thereof. In certain embodiments, the opioid is selective for the mu (μ) opioid receptor. In certain embodiments, the opioid is selective for the kappa (κ) opioid receptor. In certain embodiments, the opioid is selective for the delta (δ) opioid receptor. Opioids suitable for use can be naturally occurring, semi-synthetic or synthetic molecules.

In certain embodiments, OPIOID may be a residue of an opioid agonist of the formula:

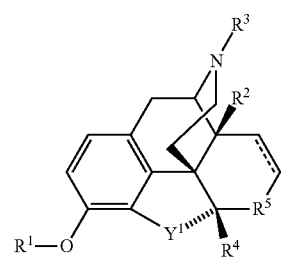

Formula I wherein:
$R^1$ is selected from hydrogen, acyl, and lower alkyl;
$R^2$ is selected from hydrogen and hydroxyl;
$R^3$ is selected from hydrogen and alkyl;
$R^4$ is hydrogen;
"———" represents an optional bond;
$Y^1$ is selected from O and S; and R⁵ is selected from the group consisting of

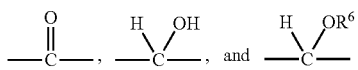

(without regard to stereochemistry), wherein R⁶ is an organic radical [including C(O)CH₃]. Exemplary R³ groups include lower alkyl such as methyl, ethyl, isopropyl, and the like, as well as the following:

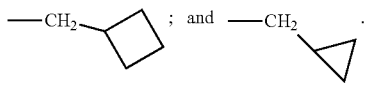

In certain embodiments, OPIOID may be a residue of an opioid agonist of the formula:

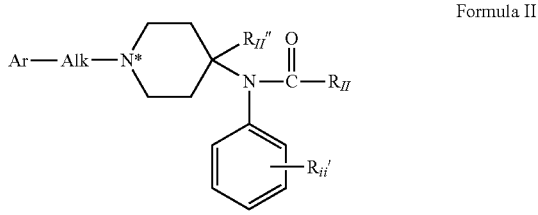

Formula II wherein:
N* is nitrogen;
Ar is selected from cyclohexyl, phenyl, halophenyl, methoxyphenyl, aminophenyl, pyridyl, furyl and thienyl;
Alk is selected from ethylene and propylene;
$R_{II}$ is selected from lower alkyl, lower alkoxy, dimethylamino, cyclopropyl, 1-pyrrolidyl, morpholino
$R_{II}'$ is selected from hydrogen, methyl and methoxy; and
$R_{II}''$ is selected from hydrogen and an organic radical.
With respect to Formula II, it will be understood that, depending on the conditions, one or both of the amines—but more typically, the amine marked with an asterisk ("N*") in Formula II—can be protonated.
In certain embodiments $R_{II}$ is selected from lower alkyl. In certain embodiments $R_{II}$ is ethyl.
Opioids that may be used include, but are not limited to, acetorphine, acetyldihydrocodeine, acetyldihydrocodeinone, acetylmorphinone, alfentanil, allylprodine, alphaprodine, anileridine, benzylmorphine, bezitramide, biphalin, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, dynorphins (including dynorphin A and dynorphin B), endorphins (including beta-endorphin and α/β-neo-endorphin), enkephalins (including Met-enkephalin and Leu-enkephalin), eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, and tramadol.

In certain embodiments, the opioid agonist is selected from hydrocodone, morphine, hydromorphone, oxycodone, codeine, levorphanol, meperidine, methadone, oxymorphone, buprenorphine, fentanyl, dipipanone, heroin, tramadol, nalbuphine, etorphine, dihydroetorphine, butorphanol, and levorphanol.

In other embodiments, the opioid agonist is selected from fentanyl, hydromorphone, nalbuphine, morphine, codeine, oxycodone, and oxymorphone.

Any other opioid compound having opioid agonist activity may also be used. Assays for determining whether a given compound (regardless of whether the compound is an opioid agonist compound disclosed herein or in the parent form) can act as an agonist on an opioid receptor are described herein and are known in the art.

In some instances, opioid agonists can be obtained from commercial sources. In addition, opioid agonists can be synthesized using standard techniques of synthetic organic chemistry. Synthetic approaches for preparing opioid agonists are described in the literature and in, for example, U.S. Pat. Nos. 2,628,962, 2,654,756, 2,649,454, and 2,806,033.

Each of these (and other) opioid agonists (or residues thereof) can be covalently attached (either directly or through one or more atoms) to a water-soluble oligomer. Methods for preparing such opioid agonist compounds are disclosed in U.S. Patent Application Publication No. 2010/0048602, International Patent Application Publication No. WO 2008/112288, International Patent Application Publication No. WO 2010/033195, U.S. Patent Application Publication No. 2011/0237614, International Patent Application Publication No. WO 2011/011543, U.S. Patent Application Publication No. 2012/0184581, International Patent Application Publication No. WO 2011/088140, and U.S. patent application Ser. No. 13/521,556. each of which are incorporated by reference. Specific and exemplary synthetic methods are recited in Examples 1-6 below.

Opioid agonists useful in the invention generally have a molecular weight of less than about 1500 Da (Daltons), and in certain embodiments less than about 1000 Da. Exemplary molecular weights of opioid agonists include molecular weights of: less than about 950 Da; less than about 900 Da; less than about 850 Da; less than about 800 Da; less than about 750 Da; less than about 700 Da; less than about 650 Da; less than about 600 Da; less than about 550 Da; less than about 500 Da; less than about 450 Da; less than about 400 Da; less than about 350 Da; and less than about 300 Da.

The opioid agonists used in the invention, if chiral, may be in a racemic mixture, or an optically active form, for example, a single optically active enantiomer, or any combination or ratio of enantiomers (i.e., scalemic mixture). In addition, the opioid agonist may possess one or more geometric isomers. With respect to geometric isomers, a composition can comprise a single geometric isomer or a mixture of two or more geometric isomers. An opioid agonist for use in the present invention can be in its customary active form, or may possess some degree of modification. For example, an opioid agonist may have a targeting agent, tag, or transporter attached thereto, prior to or after covalent attachment of a water-soluble oligomer. Alternatively, the opioid may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In certain embodiments, however, the opioid does not include attachment to a lipophilic moiety.

The opioid agonist for coupling to a water-soluble oligomer possesses a free hydroxyl, carboxyl, carbonyl, thio, amino group, or the like (i.e., "handle") suitable for covalent attachment to the oligomer. In addition, the opioid agonist can be modified by introduction of a reactive group, for example, by conversion of one of its existing functional groups to a functional group suitable for formation of a stable covalent linkage between the oligomer and the opioid agonist.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where in certain embodiments, alkyl is methyl; α-hydroxy acid, such as lactic acid or glycolic acid; phosphazene, oxazoline, amino acids, carbohydrates such as monosaccharides, saccharide or mannitol; and N-acryloylmorpholine. In certain embodiments, monomer types include alkylene oxide, olefinic alcohol, hydroxyalkyl methacrylamide or methacrylate, N-acryloylmorpholine, and α-hydroxy acid. In certain embodiments, each oligomer is, independently, a co-oligomer of two monomer types selected from this group, or, in certain embodiments, is a homo-oligomer of one monomer type selected from this group.

The two monomer types in a co-oligomer may be of the same monomer type, for example, two alkylene oxides, such as ethylene oxide and propylene oxide. In certain embodiments, the oligomer is a homo-oligomer of ethylene oxide. Usually, although not necessarily, the terminus (or termini) of the oligomer that is not covalently attached to an opioid agonist is capped to render it unreactive. Alternatively, the terminus may include a reactive group. When the terminus is a reactive group, the reactive group is either selected such that it is unreactive under the conditions of formation of the final oligomer or during covalent attachment of the oligomer to an opioid agonist, or it is protected as necessary. One common end-functional group is hydroxyl or —OH, particularly for oligoethylene oxides.

The water-soluble oligomer (e.g., "POLY" in the structures provided herein) can have any of a number of different geometries. For example, it can be linear, branched, or forked. Most typically, the water-soluble oligomer is linear or is branched, for example, having one branch point. Although much of the discussion herein is focused upon poly(ethylene oxide) as an illustrative oligomer, the discussion and structures presented herein can be readily extended to encompass any of the water-soluble oligomers described above.

The molecular weight of the water-soluble oligomer, excluding the linker portion, in certain embodiments is generally relatively low. For example, the molecular weight of the water-soluble oligomer is typically below about 2200 Daltons, and more typically at around 1500 Daltons or below. In certain other embodiments, the molecular weight of the water-soluble oligomer may be below 800 Daltons.

In certain embodiments, exemplary values of the molecular weight of the water-soluble oligomer include less than or equal to about 500 Daltons, or less than or equal to about 420 Daltons, or less than or equal to about 370 Daltons, or less than or equal to about 370 Daltons, or less than or equal to about 325 Daltons, less than or equal to about 280 Daltons, less than or equal to about 235 Daltons, or less than or equal to about 200 Daltons, less than or equal to about 175 Daltons, or less than or equal to about 150 Daltons, or less than or equal to about 135 Daltons, less than or equal to about 90 Daltons, or less than or equal to about 60 Daltons, or even less than or equal to about 45 Daltons.

In certain embodiments, exemplary values of the molecular weight of the water-soluble oligomer, excluding the linker portion, include: below about 1500 Daltons; below about 1450 Daltons; below about 1400 Daltons; below about 1350 Daltons; below about 1300 Daltons; below about 1250 Daltons; below about 1200 Daltons; below about 1150 Daltons; below about 1100 Daltons; below about 1050 Daltons; below about 1000 Daltons; below about 950 Daltons; below about 900 Daltons; below about 850 Daltons; below about 800 Daltons; below about 750 Daltons; below about 700 Daltons; below about 650 Daltons; below about 600 Daltons; below about 550 Daltons; below about 500 Daltons; below about 450 Daltons; below about 400 Daltons; and below about 350 Daltons; but in each case above about 250 Daltons.

In certain embodiments, rather than being bound to an oligomer, the opioid agonist is covalently attached to a water-soluble polymer, i.e., a moiety having a more than 50 repeating subunits. For instance, the molecular weight of the water-soluble polymer, excluding the linker portion, may be below about 80,000 Daltons; below about 70,000 Daltons; below about 60,000 Daltons; below about 50,000 Daltons; below about 40,000 Daltons; below about 30,000 Daltons; below about 20,000 Daltons; below about 10,000 Daltons; below about 8,000 Daltons; below about 6,000 Daltons; below about 4,000 Daltons; below about 3,000 Daltons; and below about 2,000 Daltons; but in each case above about 250 Daltons.

In certain embodiments, exemplary ranges of molecular weights of the water-soluble, oligomer (excluding the linker) include: from about 45 to about 225 Daltons; from about 45 to about 175 Daltons; from about 45 to about 135 Daltons; from about 45 to about 90 Daltons; from about 90 to about 225 Daltons; from about 90 to about 175 Daltons; from about 90 to about 135 Daltons; from about 135 to about 225 Daltons; from about 135 to about 175 Daltons; and from about 175 to about 225 Daltons.

In other alternative embodiments, exemplary ranges of molecular weights of the water-soluble oligomer (excluding the linker) include: from about 250 to about 1500 Daltons; from about 250 to about 1200 Daltons; from about 250 to about 800 Daltons; from about 250 to about 500 Daltons; from about 250 to about 400 Daltons; from about 250 to about 500 Daltons; from about 250 to about 1000 Daltons; and from about 250 to about 500 Daltons.

In other embodiments related to water-soluble polymer bound opioid agonists, exemplary ranges of molecular weights of the water-soluble polymer (excluding the linker) include: from about 2,000 to about 80,000 Daltons; from about 2,000 to about 70,000 Daltons; from about 2,000 to about 60,000 Daltons; from about 2,000 to about 50,000 Daltons; from about 2,000 to about 40,000 Daltons; from about 2,000 to about 30,000 Daltons; from about 2,000 to about 20,000 Daltons; from about 2,000 to about 10,000 Daltons; from about 2,000 to about 8,000 Daltons; from about 2,000 to about 6,000 Daltons; from about 2,000 to about 4,000 Daltons; from about 2,000 to about 3,000 Daltons; from about 10,000 to about 80,000 Daltons; from about 10,000 to about 60,000 Daltons; from about 10,000 to about 40,000 Daltons; from about 30,000 to about 80,000 Daltons; from about 30,000 to about 60,000 Daltons; from about 40,000 to about 80,000 Daltons; and from about 60,000 to about 80,000 Daltons.

The number of monomers in the water-soluble oligomer may be between about 1 and about 1825 (inclusive), including all integer values within this range.

In certain embodiments, the number of monomers in the water-soluble oligomer falls within one or more of the following inclusive ranges: between 1 and 5 (i.e., is selected from 1, 2, 3, 4, and 5); between 1 and 4 (i.e., can be 1, 2, 3, or 4); between 1 and 3 (i.e., selected from 1, 2, or 3); between 1 and 2 (i.e., can be 1 or 2); between 2 and 5 (i.e., can be selected from 2, 3, 4, and 5); between 2 and 4 (i.e., is selected from 2, 3, and 4); between 2 and 3 (i.e., is either 2 or 3); between 3 and 5 (i.e., is either 3, 4 or 5); between 3 and 4 (i.e., is 3 or 4); and between 4 and 5 (i.e., is 4 or 5). In a specific instance, the number of monomers in series in the oligomer (and the corresponding opioid agonist compound) is selected from 1, 2, 3, 4, or 5. Thus, for example, when the water-soluble oligomer includes $CH_3$—$(OCH_2CH_2)_n$—, "n" is an integer that can be 1, 2, 3, 4, or 5.

In certain embodiments, the number of monomers in the water-soluble oligomer falls within one or more of the following inclusive ranges: between 6 and 30 (i.e., is selected from 6, 7, 8, 9, 10, 11, 12, 13, 14, 15, 16, 17, 18, 19, 20, 21, 22, 23, 24, 25, 26, 27, 28, 29, and 30); between 6 and 25 (i.e., is selected from 6, 7, 8, 9, 10, 11, 12, 13, 14, 15, 16, 17, 18, 19, 20, 21, 22, 23, 24, and 25); between 6 and 20 (i.e., is selected from 6, 7, 8, 9, 10, 11, 12, 13, 14, 15, 16, 17, 18, 19, and 20); between 6 and 15 (is selected from 6, 7, 8, 9, 10, 11, 12, 13, 14, 15); between 6 and 10 (i.e., is selected from 6, 7, 8, 9, and 10); between 10 and 25 (i.e., is selected from 10, 11, 12, 13, 14, 15, 16, 17, 18, 19, 20, 21, 22, 23, 24, and 25); and between 15 and 20 (i.e., is selected from 15, 16, 17, 18, 19, and 20). In certain instances, the number of monomers in series in the oligomer (and the corresponding opioid agonist compound) is one of 6, 7, 8, 9, 10, 11, 12, 13, 14, 15, 16, 17, 18, 19, 20, 21, 22, 23, 24, or 25. Thus, for example, when the water-soluble oligomer includes $CH_3$—$(OCH_2CH_2)_n$—, "n" is an integer that can be 6, 7, 8, 9, 10, 11, 12, 13, 14, 15, 16, 17, 18, 19, 20, 21, 22, 23, 24, or 25.

In yet another embodiment, the number of monomers in the water-soluble oligomer falls within the following inclusive range: between 1 and 10, i.e., is selected from 1, 2, 3, 4, 5, 6, 7, 8, 9, and 10.

In certain other embodiments, the number of monomers in the water-soluble oligomer falls within one or more of the following inclusive ranges: between 35 and 1825; between 100 and 1800; between 200 and 1600; between 400 and 1400; between 600 and 1200; between 800 and 1000; between 35 and 1000; between 35 and 600; between 35 and 400; between 35 and 200; between 35 and 100; between 1000 and 1825; between 1200 and 1825; between 1400 and 1825; and between 1600 and 1825.

When the water-soluble oligomer has 1, 2, 3, 4, or 5 monomers, these values correspond to a methoxy end-capped oligo (ethylene oxide) having a molecular weight of about 75, 119, 163, 207, and 251 Daltons, respectively. When the oligomer has 6, 7, 8, 9, 10, 11, 12, 13, 14, or 15 monomers, these values correspond to a methoxy end-capped oligo (ethylene oxide) having a molecular weight of about 295, 339, 383, 427, 471, 515, 559, 603, 647, and 691 Daltons, respectively.

When the water-soluble oligomer is attached to the opioid agonist (in contrast to the step-wise addition of one or more monomers to effectively "grow" the oligomer onto the opioid agonist), the composition containing an activated form of the water-soluble oligomer may be monodispersed. In those instances, however, where a bimodal composition is employed, the composition will possess a bimodal distribution centering around any two of the above numbers of monomers. Ideally, the polydispersity index of each peak in the bimodal distribution, Mw/Mn, is 1.01 or less, and in certain embodiments, is 1.001 or less, and in certain embodiments is 1.0005 or less. In certain embodiments, each peak possesses a MW/Mn value of 1.0000. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

In certain embodiments the water-soluble oligomer is obtained from a composition that is unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble oligomers can be prepared as described in Chen and Baker, J. Org. Chem. 6870-6873 (1999), WO 02/098949, and U.S. Patent Application Publication 2005/0136031.

When present, the spacer moiety (through which the water-soluble oligomer is attached to the opioid agonist) may be a single bond, a single atom, such as an oxygen atom or a sulfur atom, two atoms, or a number of atoms. In particular, "X" may represent a covalent bond between OPIOID and POLY, or alternatively it may represent a chemical moiety not present on OPIOID and/or POLY alone. A spacer moiety is typically but is not necessarily linear in nature. In certain embodiments, the spacer moiety, "X" is hydrolytically stable, and is in certain embodiments also enzymatically stable. In certain embodiments, the spacer moiety, "X" is physiologically cleavable, i.e. hydrolytically cleavable or enzymatically degradable. In certain embodiments, the spacer moiety "X" is one having a chain length of less than about 12 atoms, and in certain embodiments less than about 10 atoms, in certain embodiments less than about 8 atoms and in certain embodiments less than about 5 atoms, whereby length is meant the number of atoms in a single chain, not counting substituents. For instance, a urea linkage such as this, $R_{oligomer}$—NH—(C=O)—NH—$R'_{OP}$, is considered to have a chain length of 3 atoms (—<u>N</u>H—<u>C</u>(O)—<u>N</u>H—). In certain embodiments, the spacer moiety linkage does not comprise further spacer groups.

In some instances, the spacer moiety "X" comprises an ether, amide, urethane, amine, thioether, urea, or a carbon-carbon bond. Functional groups are typically used for forming the linkages. The spacer moiety may also comprise (or be adjacent to or flanked by) spacer groups, as described further below.

More specifically, in certain embodiments, a spacer moiety, X, may be any of the following: "—" (i.e., a covalent bond, that may be stable or degradable, between the residue of the opioid agonist and the water-soluble oligomer), —O—, —NH—, —S—, —C(O)—, —C(O)O—, —OC(O)—, —CH$_2$—C(O)O—, —CH$_2$—OC(O)—, —C(O)O—CH$_2$—, —OC(O)—CH$_2$—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —CH$_2$—CH$_2$—CH$_2$—CH$_2$—C(O)—NH—NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, where R$^6$ is H or an organic radical selected from the group consisting of alkyl, substituted alkyl, alkenyl, substituted alkenyl, alkynyl, substituted alkynyl, aryl and substituted aryl. An exemplary linker is oxygen.

For purposes of the present disclosure, however, a group of atoms is not considered a spacer moiety when it is immediately adjacent to an oligomer segment, and the group of atoms is the same as a monomer of the oligomer such that the group would represent a mere extension of the oligomer chain.

The linkage "X" between the water-soluble oligomer and the opioid agonist is typically formed by reaction of a functional group on a terminus of the oligomer (or one or more monomers when it is desired to "grow" the oligomer onto the opioid agonist) with a corresponding functional group within the opioid agonist. For example, an amino group on an oligomer may be reacted with a carboxylic acid or an activated carboxylic acid derivative on the opioid agonist, or vice versa, to produce an amide linkage. Alternatively, reaction of an amine on an oligomer with an activated carbonate (e.g. succinimidyl or benzotriazyl carbonate) on the opioid agonist, or vice versa, forms a carbamate linkage. Reaction of an amine on an oligomer with an isocyanate (R—N=C=O) on an opioid agonist, or vice versa, forms a urea linkage (R—NH—(C=O)—NH—R'). Further, reaction of an alcohol (alkoxide) group on an oligomer with an alkyl halide, or halide group within an opioid agonist, or vice versa, forms an ether linkage. In yet another coupling approach, an opioid agonist having an aldehyde function is coupled to an oligomer amino group by reductive amination, resulting in formation of a secondary amine linkage between the oligomer and the opioid agonist.

In certain embodiments, the water-soluble oligomer is an oligomer bearing an aldehyde functional group. In this regard, the oligomer will have the following structure: CH$_3$O—(CH$_2$—CH$_2$—O)$_n$—(CH$_2$)$_p$—C(O)H, wherein (n) is one of 1, 2, 3, 4, 5, 6, 7, 8, 9 and 10 and (p) is one of 1, 2, 3, 4, 5, 6 and 7. In certain embodiments (n) values include 1, 2, 3, 4, 7, 8, 9, and 10 and (p) values 2, 3 and 4. In addition, the carbon atom alpha to the —C(O)H moiety can optionally be substituted with alkyl.

Typically, the terminus of the water-soluble oligomer not bearing a functional group is capped to render it unreactive. When the oligomer does include a further functional group at a terminus other than that intended for formation of an opioid agonist compound, that group is either selected such that it is unreactive under the conditions of formation of the linkage "X," or it is protected during the formation of the linkage "X." Such exemplary oligomeric termini include hydroxyl, alkoxy, and or a protecting group.

As stated above, the water-soluble oligomer includes at least one functional group prior to conjugation. The functional group typically comprises an electrophilic or nucleophilic group for covalent attachment to an opioid agonist, depending upon the reactive group contained within or introduced into the opioid agonist. Examples of nucleophilic groups that may be present in either the oligomer or the opioid agonist include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most opioid agonists for covalent attachment to an oligomer will possess a free hydroxyl, amino, thio, aldehyde, ketone, or carboxyl group.

Examples of electrophilic functional groups that may be present in either the oligomer or the opioid agonist include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also included are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(=O)O-Q, where Q is selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g. hydroxy, thio, or amino groups, to produce various bond types. Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the opioid agonist are utilized to prepare the opioid agonist compounds of the invention.

In certain embodiments, reactions favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e. aldehyde hydrate, hemiacetal, acetal, ketone hydrate, hemiketal, and ketal) are reacted with amines, followed by reduction of the resulting imine, if desired, to provide an amine linkage (reductive amination).

In certain embodiment, reactions favor formation of a physiologically cleavable linkage. The releasable linkages may, but do not necessarily, result in the water-soluble oligomer (and any spacer moiety) detaching from the opioid in vivo (and in some cases in vitro) without leaving any fragment of the water-soluble oligomer (and/or any spacer moiety or linker) attached to the opioid. Exemplary releasable linkages include carbonate, carboxylate ester, phosphate ester, thiolester, anhydrides, acetals, ketals, acyloxyalkyl ether, imines, certain carbamates, and orthoesters. Such linkages can be readily formed by reaction of the opioid and/or the polymeric reagent using coupling methods commonly employed in the art. Hydrolyzable linkages are often readily formed by reaction of a suitably activated oligomer with a non-modified functional group contained within the opioid.

In some instances the opioid agonist may not have a functional group suited for conjugation. In this instance, it is possible to modify the "original" opioid agonist so that it does have the desired functional group. For example, if the opioid agonist has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare an opioid agonist compound of a parent opioid agonist bearing a carboxyl group wherein the carboxyl group-bearing opioid agonist is coupled to an amino-terminated oligomeric ethylene glycol, to provide an opioid agonist compound having an amide group covalently linking the opioid agonist to the oligomer. This can be performed, for example, by combining the carboxyl group-bearing opioid agonist with the amino-terminated oligomeric ethylene glycol in the presence of a coupling reagent, (such as dicyclohexylcarbodiimide or "DCC") in an anhydrous organic solvent.

Further, it is possible to prepare an opioid agonist compound of a parent opioid agonist bearing a hydroxyl group wherein the hydroxyl group-bearing opioid agonist is coupled to an oligomeric ethylene glycol halide to result in an ether (—O—) linked opioid agonist compound. This can be performed, for example, by using sodium hydride to deprotonate the hydroxyl group followed by reaction with a halide-terminated oligomeric ethylene glycol.

In another example, it is possible to prepare an opioid agonist compound of a parent opioid agonist bearing a ketone group by first reducing the ketone group to form the corresponding hydroxyl group. Thereafter, the opioid agonist now bearing a hydroxyl group can be coupled as described herein.

In still another instance, it is possible to prepare an opioid agonist compound of a parent opioid agonist bearing an amine group. In one approach, the amine group-bearing opioid agonist and an aldehyde-bearing oligomer are dissolved in a suitable buffer after which a suitable reducing agent (e.g., NaCNBH$_3$) is added. Following reduction, the result is an amine linkage formed between the amine group of the amine group-containing opioid agonist and the carbonyl carbon of the aldehyde-bearing oligomer.

In another approach for preparing an opioid agonist compound of a parent opioid agonist bearing an amine group, a carboxylic acid-bearing oligomer and the amine group-bearing opioid agonist are combined, typically in the presence of a coupling reagent (e.g., DCC). The result is an amide linkage formed between the amine group of the amine group-containing opioid agonist and the carbonyl of the carboxylic acid-bearing oligomer.

The synthesis of certain exemplary opioid agonist compounds are described in detail Example 1, Example 2, and Example 3. Example 1 describes the synthesis of oligomeric mPEG$_n$-morphine compounds. Since morphine has two hydroxyl functions, in the synthesis employed, the non-target hydroxyl group (i.e., the aromatic hydroxyl) is first protected with a suitable protecting group such as β-methoxyethoxymethyl ether, MEM, followed by reaction of the MEM-protected morphine with oligomeric PEG-mesylate (PEG$_n$-OMs) in the presence of the strong base, sodium hydride, to introduce the oligomeric polyethylene glycol moiety. The MEM protecting group is then removed by treatment with acid, e.g., hydrochloric acid, to provide the desired 6-mPEG$_n$-O-morphine compounds (n=1, 2, 3, 4, 5, 6, 7, 9) having the generalized structure shown below:

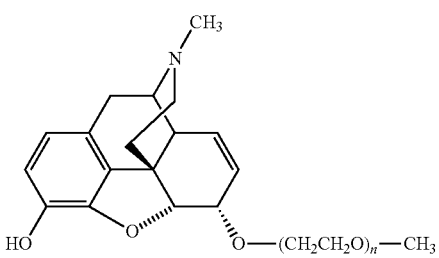

The synthesis of illustrative mPEG$_n$-O-Codeine compounds is described in detail in Example 2. In the approach employed, codeine, having a single target hydroxyl function, is reacted with mPEG$_n$ mesylate in the presence of a strong base, e.g., sodium hydride, to provide the desired compound. The products can be purified, for example, using high performance liquid chromatography (HPLC). The oliogomeric mPEG$_n$-O-Codeine compounds (n=1, 2, 3, 4, 5, 6, 7, 9) prepared have the generalized structure shown below:

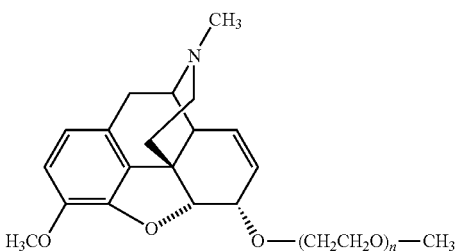

In a similar fashion, mPEG$_n$-O-hydroxycodone compounds were prepared as described in detail in Example 3 (n=1, 2, 3, 4, 5, 6, 7, 9). The compounds possess the following generalized structure:

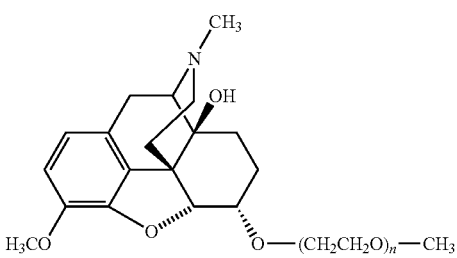

Additional compounds may be similarly prepared.

In certain embodiments of the invention, X is a stable linker. As previously disclosed, it has been found that certain opioid agonists bound to small water-soluble oligomers via a stable linkage, while retaining the ability to cross the blood-brain barrier, do so at a reduced BBB crossing rate relative to the parent opioid agonist. Without wishing to be bound by any particular theory, it is believed that the reduced BBB membrane crossing rate is a direct function of changes in the intrinsic BBB permeability properties of the molecule relative to the parent opioid agonist. Again not wishing to be bound by any particular theory, it is presumed that such opioid agonist compounds possess low addictive properties due to a slow crossing of the BBB, avoiding the rapid peak concentrations associated with the parent opioid agonists and underlying addictive highs. Additionally, the opioid agonist compounds may exhibit an improved side effect profile relative to the parent opioid due to an altered tissue distribution of the opioid in vivo or decreased activity at peripheral opioid receptors. As such, the compositions and combinations of the present invention are believed to share these properties.

Thus, any combination of opioid agonist, linker, and water-soluble oligomer may be used, provided that the opioid agonist compound is able to cross the BBB. In certain embodiments, the opioid agonist compound crosses the BBB at a reduced rate relative to the parent opioid agonist. In certain embodiments, the water-soluble oligomer is a PEG moiety. In certain embodiments the PEG-moiety consists of 1-10 polyethylene glycol units. Typically, the PEG moiety is a small monomeric PEG consisting of 1-3 (i.e. 1, 2, or 3) polyethylene glycol units. In certain embodiments the PEG moiety may be 4 or 5 or 6 polyethylene glycol units.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of most solutes and drugs into the central nervous system.

As will be understood by one of skill in the art, molecular size, lipophilicity, and PgP interaction are among the primary parameters affecting the intrinsic BBB permeability properties of a given molecule. That is to say, these factors, when taken in combination, control whether a given molecule passes through the BBB, and if so, at what rate.

Due to the small pore size within the BBB, molecular size plays a significant role in determining whether a given molecule will pass through the BBB. Very large molecules, for example a molecule having a molecular weight of 5,000 Daltons, will not cross the BBB, whereas small molecules are more likely to permeate the BBB. Other factors, however, also play a role in BBB crossing. Antipyrine and atenolol are both small molecule drugs; antipyrine readily crosses the BBB, whereas passage of atenolol is very limited, or effectively non-existent. Antipyrine is an industry standard for a high BBB permeation; atenolol is an industry standard for low permeation of the BBB. See, e.g., Summerfield et al., *J Pharmacol Exp Ther* 322:205-213 (2007). Therefore, in accordance with the invention, where X is a stable linker, opioid agonist compounds, as part of the disclosed compositions and combinations, having 1-3 polyethylene glycol units can generally be expected to cross the BBB. In certain circumstances, where the intrinsic BBB permeability properties as a whole are suitable, particular opioid agonist compounds having 4 or 5 polyethylene glycol units may also cross the BBB.

Lipophilicity is also a factor in BBB permeation. Lipophilicity may be expressed as logP (partition coefficient) or in some instances logD (distribution coefficient). The logP (or logD) for a given molecule can be readily assessed by one of skill in the art. The value for logP may be a negative number (more hydrophilic molecules) or a positive number (more hydrophobic molecules). As used herein when referring to logP, "more negative" means moving in the direction, on the logP scale, from positive to negative logP (e.g., a logP of 2.0 is "more negative" than a logP of 4.0, a logP of −2.0 is "more negative" than a logP of −1.0). Molecules having a negative logP (hydrophilic molecules) generally do not permeate the BBB. In certain embodiments, the opioid agonist compounds of the invention have a logP between about 0 and about 4.0. In certain embodiments, the opioid agonist compounds of the invention have a logP between about 1.0 and about 3.5. In certain embodiments, the opioid agonist compounds of the invention have a logP of about 4.0, of about 3.5, of about 3.0, of about 2.5, of about 2.0, of about 1.5, of about 1.0, of about 0.5, or of about 0, or they may have a logP in the range of about 0 to about 3.5, of about 0 to about 3.0, of about 0 to about 2.0, of about 0 to about 1.0, of about 1.0 to about 4.0, of about 1.0 to about 3.0, of about 1.0 to about 2.0, of about 2.0 to about 4.0, of about 2.0 to about 3.5, of about 2.0 to about 3.0, of about 3.0 to about 4.0, or of about 3.0 to about 3.5.

Permeability across the BBB is also dependent on P-glycoprotein, or PgP, an ATP-dependent efflux transporter highly expressed at the BBB. One of skill in the art can readily determine whether a compound is a substrate for PgP using in vitro methods. Compounds which are substrates for PgP in vitro likely will not permeate the BBB in vivo. Conversely, poor substrates for PgP, as assessed in vitro, are generally likely to display in vivo permeability of the BBB, provided the compound meets other criteria as discussed herein and as known to one of skill in the art. See, e.g., Tsuji, NeuroRx 2:54-62 (2005) and Rubin and Staddon, Annu. Rev. Neurosci. 22:11-28 (1999).

In certain embodiments, the water-soluble oligomer may be selected in accordance with the desired pharmacokinetic profile of the opioid agonist compound. In other words, conjugation of the opioid to a water-soluble oligomer will result in a net reduction in BBB membrane crossing rate, however the reduction in rate may vary depending on the size of the oligomer used. Generally, where a minimal reduction in BBB crossing rate is desired, a smaller oligomer may be used; where a more extensive reduction in BBB crossing rate is desired, a larger oligomer may be used. In certain embodiments, a combination of two or more different opioid agonist compounds may be administered simultaneously, wherein each opioid agonist compound has a differently sized water-soluble oligomer portion, and wherein the rate of BBB crossing for each opioid agonist compound is different due to the different oligomer sizes. In this manner, the rate and duration of BBB crossing of the opioid agonist compound can be specifically controlled through the simultaneous administration of multiple opioid agonist compounds with varying pharmacokinetic profiles.

For compounds whose degree of blood-brain barrier crossing ability is not readily known, such ability can be determined using a suitable animal model such as an in situ rat brain perfusion ("RBP") model. Briefly, the RBP technique involves cannulation of the carotid artery followed by perfusion with a compound solution under controlled conditions, followed by a wash out phase to remove compound remaining in the vascular space. (Such analyses can be conducted, for example, by contract research organizations such as Absorption Systems, Exton, Pa.). More specifically, in the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl, P., et al., J. Med. Chem. 2000, 43, 3714-3717; and Kelder, J., et al., Pharm. Res. 1999, 16, 1514-1519.

In certain embodiments, where X is a stable linker, the molecular weight of the opioid agonist compound is less than 2000 Daltons, and in certain embodiments less than 1000 Daltons. In certain embodiments, the molecular weight of the opioid agonist compound is less than 950 Daltons, less than 900 Daltons, less than 850 Daltons, less than 800 Daltons, less than 750 Daltons, less than 700 Daltons, less than 650 Daltons, less than 600 Daltons, less than 550 Daltons, less than 500 Daltons, less than 450 Daltons, or less than 400 Daltons.

In certain embodiments, where X is a stable linker, the molecular weight of X-POLY (i.e. the water soluble oligomer in combination with the linker, where present) is less than 2000 Daltons. In certain embodiments, the molecular weight of the X-POLY is less than 1000 Daltons. In certain embodiments, the molecular weight of X-POLY is less than 950 Daltons, less than 900 Daltons, less than 850 Daltons, less than 800 Daltons, less than 750 Daltons, less than 700 Daltons, less than 650 Daltons, less than 600 Daltons, less than 550 Daltons, less than 500 Daltons, less than 450 Daltons, less than 400 Daltons, less than 350 Daltons, less than 300 Daltons, less than 250 Daltons, less than 200 Daltons, less than 150 Daltons, less than 100 Daltons, or less than 50 Daltons.

In certain embodiments, where X is a stable linker, the opioid agonist compound (i.e. OPIOID-X-POLY) is less hydrophobic than the parent opioid. In other words, the logP of the opioid agonist compound is more negative than the logP of the parent opioid agonist. In certain embodiments, the logP of the opioid agonist compound is about 0.5 units more negative than that of the parent opioid agonist. In certain embodiments, the log P of the opioid agonist compound is about 4.0 units more negative, about 3.5 units more negative, about 3.0 units more negative, about 2.5 units more negative, about 2.0 units more negative, about 1.5 units more negative, about 1.0 units more negative, about 0.9 units more negative, about 0.8 units more negative, about 0.7 units more negative, about 0.6 units more negative, about 0.4 units more negative, about 0.3 units more negative, about 0.2 units more negative or about 0.1 units more negative than the parent opioid agonist. In certain embodiments, the logP of the opioid agonist compound is about 0.1 units to about 4.0 units more negative, about 0.1 units to about 3.5 units more negative, about 0.1 units to about 3.0 units more negative, about 0.1 units to about 2.5 units more negative, about 0.1 units to about 2.0 units more negative, about 0.1 units to about 1.5 units more negative, about 0.1 units to about 1.0 units more negative, about 0.1 units to about 0.5 units more negative, about 0.5 units to about 4.0 units more negative, about 0.5 units to about 3.5 units more negative, about 0.5 units to about 3.0 units more negative, about 0.5 units to about 2.5 units more negative, about 0.5 units to about 2.0 units more negative, about 0.5 units to about 1.5 units more negative, about 0.5 units to about 1.0 units more negative, about 1.0 units to about 4.0 units more negative, about 1.0 units to about 3.5 units more negative, about 1.0 units to about 3.0 units more negative, about 1.0 units to about 2.5 units more negative, about 1.0 units to about 2.0 units more negative, about 1.0 units to about 1.5 units more negative, about 1.5 units to about 4.0 units more negative, about 1.5 units to about 3.5 units more negative, about 1.5 units to about 3.0 units more negative, about 1.5 units to about 2.5 units more negative, about 1.5 units to about 2.0 units more negative, about 2.0 units to about 4.0 units more negative, about 2.0 units to about 3.5 units more negative, about 2.0 units to about 3.0 units more negative, about 2.0 units to about 2.5 units more negative. about 2.5 units to about 4.0 units more negative, about 2.5 units to about 3.5 units more negative, about 2.5 units to about 3.0 units more negative, about 3.0 units to about 4.0 units more negative, about 3.0 units to about 3.5 units more negative, or about 3.5 units to about 4.0 units more negative than the parent opioid agonist. In some embodiments, the logP of the opioid agonist compound is the same as, or is more positive than, the logP of the parent opioid agonist.

The relative permeability across the blood brain barrier and brain plasma ratio of the opioid agonist compounds has been described, for example, in International Patent Application Publication No. WO 2011/088140.

In certain embodiments, where X is a stable linker, the opioid agonist compound retains a suitable affinity for its target receptor(s), and by extension a suitable concentration and potency within the brain. In certain embodiments the opioid agonist compound binds, at least in part, to the same receptor(s) to which the parent opioid agonist binds. To determine whether the parent opioid agonist or the opioid agonist compound has activity as mu, kappa, or delta opioid receptor agonist, for example, it is possible to test such a compound. For example, a radioligand binding assay in CHO cells that heterologously express the recombinant human mu, kappa, or delta opioid receptor can be used. Briefly, cells are plated in 24 well plates and washed with assay buffer. Competition binding assays are conducted on adherent whole cells incubated with increasing concentrations of opioid agonist compounds in the presence of an appropriate concentration of radioligand. [³H]naloxone, [³H]diprenorphine and [³H]DPDPE are used as the competing radioligands for mu, kappa and delta receptors respectively. Following incubation, cells are washed, solubilized with NaOH and bound radioactivity is measured using a scintillation counter.

In certain embodiments, the Ki values of the opioid agonist compounds individually fall within the range of 0.1 to 900 nM, in certain embodiments within the range of 0.1 and 300 nM, and in certain embodiments within the range of 0.1 and 50 nM. In certain embodiments, where X is a stable linker, there is no loss of affinity of the opioid agonist compound (i.e. the OPIOID of OPIOID-X-POLY) relative to the affinity of OPIOID to its target receptor(s), and in certain embodiments the affinity of the opioid agonist compound may be greater than the affinity of OPIOID to its target receptor(s). In certain embodiments, where X is a stable linker, the affinity of the opioid agonist compound (i.e. the OPIOID of OPIOID-X-POLY) is reduced minimally relative to the affinity of OPIOID to its target receptor(s), and in some cases may even show an increase in affinity or no change in affinity. In certain embodiments, there is less than about a 2-fold loss of affinity of the opioid agonist compound relative to the affinity of the parent opioid agonist for its target receptor(s). In certain embodiments, there is less than about a 5-fold loss, less than about a 10-fold loss, less than about a 20-fold loss, less than about a 30-fold loss, less than about a 40-fold loss, less than about a 50-fold loss, less than about a 60-fold loss, less than about a 70-fold loss, less than about an 80-fold loss, less than about a 90-fold loss, or less than about a 100-fold loss of affinity of the opioid agonist compound relative to the affinity of the parent opioid agonist for its target receptor(s).

In certain other embodiments where X is a stable linker, the reduction in affinity of the opioid agonist compound relative to the affinity of the parent opioid agonist for its target receptor(s) is less than 20%. In certain embodiments, the reduction in affinity of the opioid agonist compound relative to the parent opioid is less than 10%, less than 30%, less than 40%, less than 50%, less than 60%, less than 70%, less than 80%, less than 90%, or less than 95%.

In certain embodiments where X is a stable linker, the rate of crossing the BBB, or the permeability of the opioid agonist compound is less than the rate of crossing of OPIOID alone. In certain embodiments, the rate of crossing is at least about 50% less than the rate of OPIOID alone. In certain embodiments, there is at least about a 10% reduction, at least about a 15% reduction, at least about a 20% reduction, at least about a 25% reduction, at least about a 30% reduction, at least about a 35% reduction, at least about a 40% reduction, at least about a 45% reduction, at least about a 55% reduction, at least about a 60% reduction, at least about a 65% reduction, at least about a 70% reduction, at least about a 75% reduction, at least about an 80% reduction, at least about an 85% reduction, at least about a 90% reduction at least about a 95% reduction, or at least about a 99% reduction in the BBB crossing rate of the opioid agonist compound relative to the rate of crossing of OPIOID alone. In other embodiments, the opioid agonist compounds of the invention may exhibit a 10-99% reduction, a 10-50% reduction, a 50-99% reduction, a 50-60% reduction, a 60-70% reduction, a 70-80% reduction, an 80-90% reduction, or a 90-99% reduction in the BBB crossing rate of the opioid agonist compound relative to the rate of crossing of OPIOID alone.

The opioid agonist compounds used in the present compositions and combinations, where X is a stable linker, may exhibit a 1 to 100 fold reduction in the BBB crossing rate relative to the rate of crossing of the OPIOID alone. In certain embodiments, there may be at least about a 2-fold loss, at least about a 5-fold loss, at least about a 10-fold loss, at least about a 20-fold loss, at least about a 30-fold loss, at least about a 40-fold loss, at least about a 50-fold loss, at least about a 60-fold loss, at least about a 70-fold loss, at least about an 80-fold loss, at least about a 90-fold loss, or at least about a 100-fold loss in the BBB crossing rate of the opioid agonist compound relative to the BBB crossing rate of the parent opioid agonist.

The rate of BBB crossing of the opioid agonist compounds, where X is a stable linker, may also be viewed relative to the BBB crossing rate of antipyrine (high permeation standard) and/or atenolol (low permeation standard). It will be understood by one of skill in the art that implied in any reference to BBB crossing rates of the opioid agonist compounds of the invention relative to the BBB crossing rate of antipyrine and/or atenolol is that the rates were evaluated in the same assay, under the same conditions. Thus, in certain embodiments opioid agonist compounds used herein may exhibit at least about a 2-fold lower, at least about a 5-fold lower, at least about a 10-fold lower, at least about a 20-fold lower, at least about a 30-fold lower, at least about a 40-fold lower, at least about a 50-fold lower, at least about a 60-fold lower, at least about a 70-fold lower, at least about an 80-fold lower, at least about a 90-fold lower, or at least about a 100-fold lower rate of BBB crossing rate relative to the BBB crossing rate of antipyrine. In other embodiments, the opioid agonist compounds of the invention, may exhibit at least about a 2-fold greater, at least about a 5-fold greater, at least about a 10-fold greater, at least about a 20-fold greater, at least about a 30-fold greater, at least about a 40-fold greater, at least about a 50-fold greater, at least about a 60-fold greater, at least about a 70-fold greater, at least about an 80-fold greater, at least about a 90-fold greater, or at least about a 100-fold greater rate of BBB crossing rate relative to the BBB crossing rate of atenolol.

In certain embodiments, where X is a stable linker, the opioid agonist compound (i.e. OPIOID-X-POLY) may retain all or some of the opioid agonist bioactivity relative to the parent opioid (i.e. OPIOID). In certain embodiments, the opioid agonist compound retains all the opioid agonist bioactivity relative to the parent opioid, or in some circumstances, is even more active than the parent opioid. In certain embodiments, the opioid agonist compounds used herein exhibit less than about a 2-fold decrease, less than about a 5-fold decrease, less than about a 10-fold decrease, less than about a 20-fold decrease, less than about a 30-fold decrease, less than about a 40-fold decrease, less than about a 50-fold decrease, less than about a 60-fold decrease, less than about a 70-fold decrease, less than about an 80-fold decrease, less than about a 90-fold decrease, or less than about a 100-fold decrease in bioactivity relative to the parent opioid agonist. In some embodiments, the opioid agonist compound retains at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 75%, at least 80%, at least 85%, at least 90%, or at least 95% of the opioid agonist bioactivity relative to the parent opioid.

It will be understood by one of skill in the art that the values recited herein are exemplary and non-limiting, and that certain opioid agonist compounds may fall outside the ranges recited herein yet remain within the spirit and scope of the invention. Opioid agonist compounds may be prepared and tested as a matter of routine experimentation for one of skill in the art. In particular, opioid agonists, bound to a water-soluble oligomer via a stable linkage, may be tested for penetration of the blood brain barrier as described above. Thus one of skill in the art can readily ascertain whether an opioid agonist compound is able to cross the BBB.

While it is believed that the full scope of the opioid agonist compounds of these embodiments of the invention has been described, an optimally sized oligomer can be determined as follows.

First, an oligomer obtained from a monodisperse or bimodal water-soluble oligomer is coupled to the opioid agonist through a stable linkage. Next, in vitro retention of activity is analyzed. The ability of the opioid agonist compound to cross the blood-brain barrier is then determined using an appropriate model and compared to that of the unmodified parent opioid agonist. If the results are favorable, that is to say, if, for example, the rate of crossing is reduced to an appropriate degree, then the bioactivity of opioid agonist compound is further evaluated. In certain embodiments, the compounds according to the invention maintain a significant degree of bioactivity relative to the parent opioid agonist, i.e., greater than about 30% of the bioactivity of the parent opioid agonist, or greater than about 50% of the bioactivity of the parent opioid agonist. In certain embodiments, the opioid agonist compound is orally bioavailable.

The above steps are repeated one or more times using oligomers of the same monomer type but having a different number of subunits and the results are compared.

For each opioid agonist compound whose ability to cross the blood-brain barrier is appropriately reduced in comparison to the parent opioid agonist, its oral bioavailability is then assessed. Based upon these results, that is to say, based upon the comparison of opioid agonist compounds having oligomers of varying size to a given opioid agonist at a given position or location within the opioid agonist, it is possible to determine the size of the oligomer most effective in providing an opioid agonist compound having an optimal balance between appropriate reduction in biological membrane crossing, oral bioavailability, and bioactivity. The small size of the oligomers makes such screenings feasible, and allows one to effectively tailor the properties of the resulting opioid agonist compound. By making small, incremental changes in oligomer size, and utilizing an experimental design approach, one can effectively identify an opioid agonist compound having a favorable balance of reduction in biological membrane crossing rate, bioactivity, and oral bioavailability. In some instances, attachment of an oligomer as described herein is effective to actually increase oral bioavailability of the opioid agonist.

For example, one of ordinary skill in the art, using routine experimentation, can determine a best suited molecular size and linkage for improving oral bioavailability by first preparing a series of oligomers with different weights and functional groups and then obtaining the necessary clearance profiles by administering the opioid agonist compounds to a patient and taking periodic blood and/or urine sampling. Once a series of clearance profiles have been obtained for each tested opioid agonist compound, a suitable opioid agonist compound can be identified.

Animal models (rodents and dogs) can also be used to study oral drug transport. In addition, non-in vivo methods include rodent everted gut excised tissue and Caco-2 cell monolayer tissue-culture models. These models are useful in predicting oral drug bioavailability.

In certain embodiments of the invention, X is a physiologically cleavable linker. As disclosed in the art, it has been found that certain opioids bound to small water-soluble oligomers via a cleavable linkage are unable to cross the BBB, and therefore exhibit a net reduced BBB membrane crossing rate due to slow physiological cleavage of the opioid from the water-soluble oligomer. In particular, X may be selected in accordance with the desired pharmacokinetic profile of the parent opioid agonist. In other words, conjugation of the opioids to a water-soluble oligomer will result in a net reduction in BBB membrane crossing rate, however the reduction in rate may vary depending on the linker used. Where a minimal reduction in BBB crossing rate is desired, X may be a rapidly degraded linker; where an extensive reduction in BBB crossing rate is desired, X may be a more slowly degraded linker. In certain embodiments, a combination of two or more different opioid agonist compounds may be administered simultaneously, wherein each opioid agonist compound has a different linker X, and wherein the rate of degradation of each X is different. In other words, for each different compound, the opioid will be cleaved from the water-soluble oligomer at a different rate, resulting in different net BBB membrane crossing rates. A similar effect may be achieved through the use of multifunctional water-soluble oligomers having two or more sites of opioid attachment, with each opioid linked to the water-soluble oligomer through linkers having varying rates of degradation. In this manner, the rate and duration of BBB crossing of the opioid agonist compound can be specifically controlled through the simultaneous administration of multiple opioid agonist compounds with varying pharmacokinetic profiles.

Not wishing to be bound by any particular theory, it is presumed that such opioid agonist compounds possess low addictive properties due to the net slow crossing of the BBB (due to slow physiological cleavage following administration of the opioid agonist compound), avoiding the rapid peak concentrations associated with parent opioid agonists and underlying addictive highs. Again, not wishing to be bound by any particular theory, it is believed that the opioid agonist compounds of the invention circulate in the plasma, and are cleaved in vivo at a rate dependent upon the specific cleavable linker used (and, for enzymatically degradable linkers, enzyme concentration and affinity), such that the concentration of the parent opioid circulating in the periphery is generally very low due to the slow rate of cleavage. Once cleavage has occurred, the parent opioid may travel to the brain to cross the BBB; the slow release of the parent opioid through cleavage results in a net slow delivery of the parent opioid to the brain. Additionally, the opioid agonist compounds of the present invention exhibit an improved side effect profile relative to the parent opioid dues to an altered tissue distribution of the opioid in vivo and altered receptor interaction at the periphery.

Moreover, in accordance with these embodiments of the invention, any combination of opioid, linker, and water-soluble oligomer may be used, provided that the opioid agonist compound is not able to cross the BBB or only a small fraction of the opioid agonist compound, in certain embodiments less than 5% of that administered, is able to cross the BBB. In certain embodiments, the opioid agonist compound is not able to cross the BBB. In certain embodiments, the opioid portion of the molecule, due to physiological cleavage of the opioid agonist compound, crosses the BBB at a net reduced rate relative to the parent opioid agonist. In certain embodiments, the water-soluble oligomer is a PEG moiety. In certain embodiments, the PEG moiety is a small monomeric PEG consisting of at least 6 polyethylene glycol units, preferably 6-35 polyethylene glycol units. In certain embodiments, the PEG moiety may be 6-1825 polyethylene glycol units.

In certain embodiments, where X is a physiologically cleavable linker, the opioid agonist compound (i.e. OPIOID-X-POLY) may or may not be bioactive. In certain embodiments, the opioid agonist compound is not bioactive. Such an opioid agonist compound is nevertheless effective when administered in vivo to a mammalian subject in need thereof, due to release of the opioid from the opioid agonist compound subsequent to administration. In certain embodiments, the opioid agonist compounds of the invention exhibit greater than about a 10-fold decrease, greater than about a 20-fold decrease, greater than about a 30-fold decrease, greater than about a 40-fold decrease, greater than about a 50-fold decrease, greater than about a 60-fold decrease, greater than about a 70-fold decrease, greater than about an 80-fold decrease, greater than about a 90-fold decrease, greater than about a 95-fold decrease, greater than about a 97-fold decrease, or greater than about a 100-fold decrease in bioactivity relative to the parent opioids. In some embodiments, the opioid agonist compound retains less than 1%, less than 2%, less than 3%, less than 4%, less than 5%, less than 10%, less than 15%, less than 20%, less than 25%, less than 30%, less than 35%, less than 40%, less than 50%, less than 60%, less than 70%, less than 80% or less than 90% of the opioid agonist bioactivity relative to the parent opioid.

In certain embodiments where X is a physiologically cleavable linker, the affinity of OPIOID-X-POLY for the opioid target receptor is substantially reduced relative to the affinity of OPIOID to its target receptor. In certain embodiments, there is at least about a 2-fold loss of affinity of the opioid agonist compound relative to the affinity of the parent opioid or its target receptor(s). In certain embodiments, there is at least about a 5-fold loss, at least about a 10-fold loss, at least about a 20-fold loss, at least about a 30-fold loss, at least about a 40-fold loss, at least about a 50-fold loss, at least about a 60-fold loss, at least about a 70-fold loss, at least about an 80-fold loss, at least about a 90-fold loss, or at least about a 100-fold loss of affinity of the opioid agonist compound relative to the affinity of the parent opioid agonist for its target receptor(s).

In certain embodiments where X is a physiologically cleavable linker, the reduction in affinity of the opioid agonist compound relative to the affinity of the parent opioid for its target receptor(s) is at least 20%. In certain embodiments, the reduction in affinity of the opioid agonist compound relative to the parent opioid is at least 10%, at least 30%, at least 40%, at least 50%, at least 60%, at least 70%, at least 80%, at least 90%, or at least 95%.

As previously noted, in certain embodiments where X is a physiologically cleavable linker, the opioid agonist compound is not bioactive. Such an opioid agonist compound represents a prodrug, where the compound as administered is inactive, and is made active subsequent to administration through physiological processes. Thus, in certain embodiments, the invention provides a prodrug comprising an opioid agonist reversibly attached via a covalent bond to a releasable moiety, wherein a given molar amount of the prodrug administered to a patient exhibits a rate of accumulation and a $C_{max}$ of the opioid agonist in the central nervous system in the mammal that is less than the rate of accumulation and the $C_{max}$ of an equal molar amount of the opioid agonist had the opioid agonist not been administered as part of a prodrug. The releasable moiety may be a water-soluble oligomer, and in certain embodiments is a polyethylene glycol oligomer. The agonist may be a mu, kappa, or delta opioid agonist.

In certain embodiments of the invention, X is a physiologically cleavable linker and POLY is a small monomeric PEG consisting of 1-5 (i.e. 1, 2, 3, 4, or 5) polyethylene glycol units, and in certain embodiments, 1-3 (i.e. 1, 2, or 3) polyethylene glycol units. Such compounds are small enough to cross the blood-brain barrier, but do so at a reduced membrane crossing rate relative to the parent opioid, and as such possess low addictive properties as previously discussed. In certain embodiments, X is selected to provide for cleavage of the linker and release of the opioid agonist subsequent to crossing the BBB. Alternatively, cleavage of the linker may happen both prior to, and after, crossing the BBB; in this manner the rate and duration of BBB crossing of the opioid agonist and/or opioid agonist compound can be specifically controlled.

Under the World Health Organization nomenclature, dependence syndrome (also referred to as withdrawal syndrome) is defined as a state, psychic and sometimes also physical, resulting from the interaction between a living organism and a drug, characterized by behavioral and other responses that always include a compulsion to take the drug on a continuous or periodic basis in order to experience its psychic effects, and sometimes to avoid the discomfort of its absence (WHO Expert Committee on Drug Dependence. 28th Report. Geneva, Switzerland: WHO 1993). The International Classification of Diseases or ICD-10 uses a slightly different standard to assess dependence syndrome (WHO. The ICD-10 Classification of Mental and Behavioral Disorders: Clinical Descriptions and Diagnostic Guidelines. Geneva, Switzerland: WHO, 1992). The ICD-10 uses the term "dependence syndrome" when at least 3 of the 6 features are identified with dependence syndrome. Of the six criteria, four relate to compulsivity: i) a persistent, strong desire to take a drug; ii) difficulty controlling drug use; iii) impairment of function, including neglect of pleasures and interests; and iv) harm to self. The remaining two factors relate to evidence of withdrawal symptoms and tolerance.

Studies to assess potential opioid misuse in humans may be carried out using, for example, one or more screening questionnaires designed to screen for such risk of opioid medication misuse. A number of screening tests have been developed to assess a patients' susceptibility to drug misuse or current misuse, abuse, or addition to opioid drugs. An overview of such screening tests is provided in Manchikanti, L., et al., *Pain Physician* 2008; Opioids Special Issue: 11:S155-S180. Any one or more of the screening tests described therein may be useful in evaluating a patient's tendency towards or current abuse of opioid drugs in the management and treatment of pain. One particularly useful tool to predict potential substance misuse in pain patients is described in Atluri and Sudarshan (Atluri SL, Sudarshan, G. Pain Physician 2004; 7:333-338). Another example of a useful screening tool is the Pain Medication Questionnaire or PMQ (Adams, L., 27 et al., *J. Pain and Symptom Management*, (5), 440-459 (2004)), among others. Commonly used criteria for evaluation of drug abuse include an evaluation of excessive opioid needs (e.g., multiple dose escalations, multiple emergency room visits, multiple calls to obtain more opiates, and the like), deception or lying to obtain controlled substances, current or prior doctor shopping, etc. Also indicative of a potential for addiction or abuse is the exaggeration of pain by the subject, or an unclear etiology of the pain.

One biological method for screening or monitoring opioid use is urine analysis. Although opioid testing may be carried out on urine, serum, or for example, hair, urine analysis is typically carried out due to its relatively good specificity, sensitivity, ease of administration, and cost. Such screening can be carried out at the beginning of treatment to establish a baseline, and/or to detect the presence of opioids and/or other drugs, and during the course of treatment to ensure compliance (i.e., to detect the prescribed medication), or misuse (i.e., overuse) of the prescribed medication, and to identify substances that are not to be expected in the urine. Two illustrative urine drug tests that may be used include immunoassay drug testing ("dipstick testing") and laboratory-based specific drug identification using gas chromatography/mass spectrometry and high performance liquid chromatography. Any of a variety of acceptable monitoring methods may be used to assess the potential for abuse/addiction potential of the subject opioid agonist compounds and compositions comprising the subject opioid agonist compounds.

In addition to demonstrating analgesic activity, the opioid agonist compounds used herein advantageously display very low abuse potential in preclinical studies in monkeys and in rats using self-administration and drug discrimination protocols as described in International Patent Application Publication No. WO 2011/088140. As described therein, squirrel monkeys with indwelling intravenous (IV) catheters were trained in standard lever-press methods using morphine prior to testing with test articles using a schedule of reinforcement in daily sessions of 90 minutes. Dose-related effects of the test articles were examined, using two or more doses of each drug in 3-4 subjects in a double alternation schedule in which each unit dose (or vehicle) was used in two consecutive sessions before a change in unit dose. In the self-administration studies in monkeys, the illustrative oligomeric PEG opioid agonist compound, $mPEG_6$-O-hydroxycodone, displayed significantly lower potency than oxycodone and morphine, and showed a marked reduction in reinforcing strength at the highest doses tested of 3.2 mg/kg/injection. Specifically, morphine and oxycodone produced 100% injection lever responses (% ILR) at doses of 0.03 mg/kg/injection and 0.1 mg/kg/injection, respectively. By contrast, the oligomeric mPEG-opioid agonist compound produced exclusive injection lever responding in only two subjects at the highest dose tested, 3.2 mg/kg/injection. The compound produced 22%, 39% and 50% ILR at 0.32, 1.0 and 3.2 mg/kg, respectively.

Additionally, as described in International Patent Application Publication No. WO 2011/088140, in the three-day rat substitution tests, rats trained to self-administer cocaine were exposed to saline or test article via intravenous bolus infusions for one hour sessions on three consecutive days. A compound was considered to exhibit reinforcing properties if animals maintained lever press responding with less than 20% variability over three consecutive sessions. Progressive ratio studies were performed by progressively increasing the number of lever presses needed to result in drug delivery and the break point is defined as the number of lever-presses at which the animal no longer presses in order to achieve the drug reward.

In self-administration studies in rats, the representative compound, $mPEG_6$-O-hydroxycodone, produced no behavioral evidence of positive reinforcement when tested at doses of up to 3.2 mg/kg/injection, using three-day substitution tests and progressive ratio tests on cocaine-trained animals. The PEG-opioid agonist compound showed no reinforcing properties and behaved like saline in progressive ratio tests in rats. Five out of six tested doses of the compound generated progressive ratio breakpoints lower than that produced by saline. By contrast, the maintenance dose of cocaine (0.56 mg/kg/infusion) produced a breakpoint of 128 responses for the delivery of a single bolus of drug. Likewise, hydrocodone, at a dose of 0.18 mg/kg/infusion, produced a breakpoint of 114, whereas oxycodone at test doses of 0.01 and 0.032 mg/kg/infusion produced mean breakpoints respectively of 56 and 79.

Thus, the opioid agonist compounds used herein, in addition to demonstrating antinociceptive properties, demonstrate a marked reduction in self-administration in primates, which is a key indicator of abuse liability for drugs. It is expected that when combined with a second analgesic, these properties will remain present. In one or more of the methods provided herein, an opioid agonist compound in combination with an analgesic, is characterized as producing a measurable reduction in addiction potential over the parent opioid agonist when valuated in an in-vivo self-administration model in rodents or primates as described in International Patent Application Publication No. WO 2011/088140.

The opioid agonist compounds described herein, in addition to possessing analgesic properties, and having the ability to reduce addiction/abuse potential associated with administration of opioids, have been discovered to also reduce one or more CNS side-effects typically associated with administration of opioid drugs. As such, it is believed that those properties will remain when the opioid agonist compounds are administered in combination with an analgesic. Thus, provided herein is a method for reducing one or more CNS-side effects related to the administration of an opioid analgesic drug by administering an opioid agonist compound as provided herein in combination with an analgesic. Also provided herein is a method for reducing the addiction potential and simultaneously reducing one or more CNS-side effects related to administration of an opioid analgesic drug by administering to a subject suffering from pain a therapeutically effective amount of an opioid agonist compound as provided herein in combination with an analgesic.

In one or more embodiments of the method(s), an opioid agonist compound as provided herein is considered to be effective in reducing one or more CNS-related side effects related to administration of the opioid analgesic drug if the opioid agonist compound exhibits a ten-fold or greater reduction in at least one CNS-related side effect associated with administration of the parent opioid agonist when evaluated in a mouse or other suitable animal model at an equivalent dose, wherein the one or more CNS-related side effects/elicited behaviors is selected from straub tail response, locomotor ataxia, tremor, hyperactivity, hypoactivity, convulsions, hindlimb splay, muscle rigidity, pinna reflex, righting reflex and placing. As such, it is believed that those properties will remain when the opioid agonist compounds are administered in combination with an analgesic. One particularly useful indicator for CNS activity is the straub-tail response, although any of the other herein described indicators may be used as well. In certain embodiments, compounds will exhibit a 10- to 100-fold decrease in CNS activity for a given behavior, e.g., will exhibit at least a 15-fold, or at least a 20-fold, or at least a 25-fold, or at least a 30-fold, or at least a 40-fold, or at least a 50-fold, or at least a 60-fold, or at least a 70-fold, or at least an 80-fold, or at least a 90-fold, or a 100-fold or greater decrease in CNS activity for one of the indicative behaviors observed. International Patent Application Publication No. WO 2011/088140 provides a summary of reduction of CNS activity related to a given behavior for the particular oligomeric-PEG opioid agonist compounds investigated. As can be seen from the data presented therein, significant reductions in CNS-related behaviors were observed for each of the oligomeric-PEG opioids.

As a reference, the illustrative PEG-opioid agonist compounds evaluated in International Application Publication No. WO 2011/088140 demonstrate striking advantages in terms of significantly reduced CNS side effects, even when administered at a dose correlated with maximal analgesic effect. CNS side effects that may accompany administration of opioids include cognitive failure, organic hallucinations, respiratory depression, sedation, myoclonus (involuntary twitching), and delirium, among others. When assessing one or more of the foregoing side-effects, the physician should ideally evaluate the patient to exclude other underlying etiologies. As such, the compositions and combinations described herein may be used to reduce one or more CNS side-effects related to administration of an opioid analgesic by administering the opioid agonist compound in combination with an analgesic. In one embodiment of the method, the amount of opioid agonist compound administered results in both an analgesic effect and a reduction of one or more central nervous system side effects associated with administration of the parent opioid agonist in a mammalian subject. In one or more related embodiments, the method further comprises monitoring the patient over the course of treatment for the existence and or absence of one or more CNS-side effects associated with administration of the opioid analgesic. In the event the existence of one or more CNS-side effects is observed, the monitoring may further comprise an assessment of the degree of the CNS-side effect. The monitoring may then further comprise a comparison of the degree or magnitude of the reduced CNS-side effect relative to the degree or magnitude of such CNS-side effect associated with the administration of the unmodified opioid agonist.

One advantage of administering the compositions and combinations of the present invention is that a reduction in speed of delivery of the opioid agonist to the brain is achieved, thus avoiding the rapid peak concentrations associated with the parent opioid agonists and underlying addictive highs. Moreover, based on the covalent modification of the opioid agonist molecule, the compounds of the invention are not subject to the risk of physical tampering that allows for the recovery and abuse of the rapid acting opioid agonists associated with certain alternative delivery forms intended to provide, in vivo, a reduced BBB crossing rate. As such, the opioid agonist compounds of the invention possess low addictive, anti-abuse properties. The desired pharmacokinetic properties of the opioid agonist compounds may be modulated by selecting the oligomer molecular size, linkage, and position of covalent attachment to the opioid agonist. One of ordinary skill in the art can determine the ideal molecular size of the oligomer based upon the teachings herein.

As previously described, the present disclosure relates to compositions and combinations comprising an opioid agonist compound (e.g. of the formula: OPIOID-X-POLY) and an analgesic compound. Analgesic compound generally refers to and is meant to encompass certain drugs that are used to alleviate pain. Specific analgesics listed herein are meant to be exemplary and not to limit the invention as such.

In certain embodiments, the analgesic compound is a non-steroidal anti-inflammatory drug (NSAID). NSAIDs are generally used for the relief of symptomatic pain, such as muscoskeletal pain, inflammatory relief, and other diseases or conditions such as headache, fever, postoperative pain, etc. In certain embodiments, the analgesic is an antipyretic drug. In certain embodiments, the analgesic is chosen from acetylsalicylic acid, choline salicylate, celecoxib, diclofenac, diclofenac potassium, diclofenac sodium, diclofenac sodium/misoprostol, diflunisal, etodolac, fenoprofen calcium, flurbiprofen, ibuprofen, indomethacin, ketoprofen, magnesium salicylate, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium, valdecoxib, choline magnesium trisalicylate, and ketorolac. In certain embodiments, the analgesic is chosen from ketorolac, ibuprofen, oxaprozin, indomethecin, etodolac, meloxicam, sulindac, diclofenac, flufenamic acid, difunisal, naproxen, flurbiprofen, ketoprofen, and fenoprofen. In certain embodiments, the analgesic is selected from ketorolac, ibuprofen, oxaprozin, indomethecin, etodolac, sulindac, diclofenac, flufenamic acid, difunisal, naproxen, flurbiprofen, ketoprofen, fenoprofen, and acetaminophen. In certain embodiments the analgesic compound is diclofenac.

In certain embodiments, the analgesic compound is not an opioid antagonist. In certain embodiments, the analgesic compound is not an opioid agonist.

As disclosed herein, the present compositions comprise an opioid agonist compound (e.g. of the formula: OPIOID-X-POLY) and an analgesic compound. In certain embodiments, the analgesic compound is an analgesic compound other than the parent opioid that is represented by OPIOID (or a residue thereof). In other words, for example, in certain embodiments, when OPIOID is a codeine moiety bound to X-POLY, the analgesic is not codeine (or a residue thereof).

The compositions and combinations provided herein are useful in the treatment of pain. Generally, treatment comprises administering an analgesically effective amount of an opioid agonist compound (e.g. a compound having a formula OPIOID-X-POLY) and an analgesic as disclosed herein above, either as part of a composition or as a combination. Generally, such treatment is for the management of pain (e.g., acute or chronic pain). The compositions and combinations provided herein may, for example, be used to treat nociceptive pain. The compositions and combinations provided herein may, for example, be used to treat visceral pain, musculo-skeletal pain, nerve pain, and/or sympathetic pain. Representative studies demonstrating the ability of the opioid agonist compounds to reduce or prevent pain are provided in at least U.S. Patent Application Publication No. 2010/0048602, International Patent Application Publication No. WO 2008/112288, International Patent Application Publication No. WO 2010/033195, U.S. Patent Application Publication No. 2011/0237614, International Patent Application Publication No. WO 2011/011543, U.S. Patent Application Publication No. 2012/0184581, International Patent Application Publication No. WO 2011/088140, and U.S. patent application Ser. No. 13/521,556. Administration of the compositions and combinations provided herein may, for example, be used in the treatment of chronic pain ranging from moderate to severe, including neuropathic pain. Neuropathic pain is pain due to nerve injury, neurologic disease, or the involvement of nerves due to other disease processes. The compositions and combinations described herein may be used in the treatment of pain associated with any of a number of conditions such as cancer, fibromyalgia, lower back pain, neck pain, sciatica, osteoarthritis, and the like. The compositions and combinations may also be used for relieving breakthrough pain.

All articles, books, patents, patent publications and other publications referenced herein are hereby incorporated by reference in their entireties.

It is to be understood that while the invention has been described in conjunction with certain and specific embodiments, the foregoing description as well as the examples that follow are intended to illustrate and not limit the scope of the invention. Other aspects, advantages and modifications within the scope of the invention will be apparent to those skilled in the art to which the invention pertains.

EXAMPLES

All chemical reagents referred to in the appended examples are commercially available unless otherwise indicated. The preparation of PEG-mers is described in, for example, U.S. Patent Application Publication No. 2005/0136031. Additionally, opioid agonist compound may be prepared as disclosed in U.S. Patent Application Publication No. 2010/0048602. Examples 1-3 are a reproduction of Examples 15-17 from U.S. Patent Application Publication No. 2010/0048602. Examples 4-6 are a reproduction of Examples 11-13 from U.S. Patent Application Publication No. 2010/0048602.

Example 1

Preparation of mPEG$_n$-O-Morphine Compounds

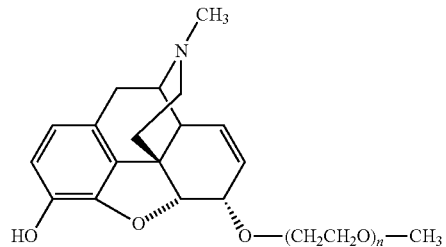

The following describes the preparation of free base using commercially available morphine sulfate hydrate (generally procedure).

Morphine sulfate USP from Spectrum (510 mg) was dissolved in water (70 ml). The solution was then basified to pH 10 using aqueous K$_2$CO$_3$ to give a white suspension. To the white suspension DCM (dichloromethane, 50 ml) was added, but failed to dissolve the solid. The mixture was made acidic with 1M HCl to result in clear biphasic solution. The organic phase was split off and the aqueous phase was carefully brought to pH 9.30 (monitored by a pH meter) using the same solution of K$_2$CO$_3$ as above. A white suspension resulted again. The heterogeneous mixture was extracted with DCM (5×25 ml) and an insoluble white solid contaminated both the organic and aqueous layers. The organic layer was dried with MgSO$_4$, filtered and rotary evaporated to yield 160 mg of morphine free base (56% recovery). No additional product was recovered from the filter cake using MeOH, but another 100 mg was recovered from the aqueous phase by 2×50 ml extraction with EtOAc to give a combined yield of 260 mg (68%).

MEM Protection of Morphine Free Base

The general approach for protecting the free base of morphine with the protecting group β-methoxyethoxymethyl ether ("MEM") is schematically shown below.

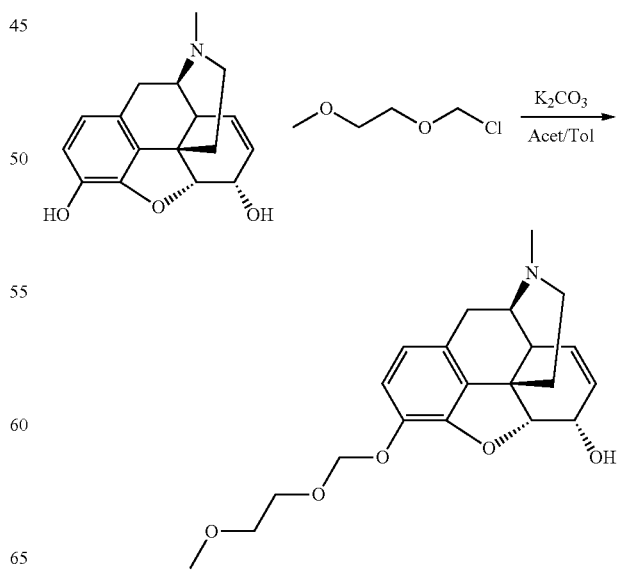

Free base morphine (160 mg, 0.56 mmol) was dissolved in 20 ml of Acetone/Toluene (2/1 mixture). To the resulting solution was added K$_2$CO$_3$ (209 mg, 1.51 mmol, 2.7 eq) followed by MEMCl (96 μl, 0.84 mmol, 1.5 eq) and the resulting heterogeneous mixture was stirred overnight at room temperature. After five hours at room temperature, the reaction was deemed complete by LC-MS. Morphine free base retention time under standard six minute gradient run conditions (std 6 min Onyx Monolyth C18 column, 50×4.6 mm; 0 to 100% Acetonitrile 0.1% TFA in Water 0.1% TFA, 1.5 ml/min; detection: UV254, ELSD, MS; retention times are quoted for UV254 detector, ELSD has about 0.09 min delay and MS has about 0.04 min delay relative to UV) was 1.09 min; retention time for product 1.54 min (std 6 min), major impurity 1.79 min. The reaction mixture was evaporated to dryness, dissolved in water, extracted with EtOAc (3×, combined organic layer washed with brine, dried over MgSO$_4$, filtered and rotary evaporated) to give 160 mg (77%) of the desired product as a colorless oil. Product purity was estimated to be about 80% by UV254.

Direct MEM Protection of Morphine Sulfate (General Procedure)

The general approach for protecting morphine sulfate with the protecting group β-methoxyethoxymethyl ether ("MEM") is schematically shown below. Although not explicitly shown in the scheme below, morphine is actually morphine sulfate hydrate, morphine.0.5 H$_2$SO$_4$.2.5 H$_2$O.

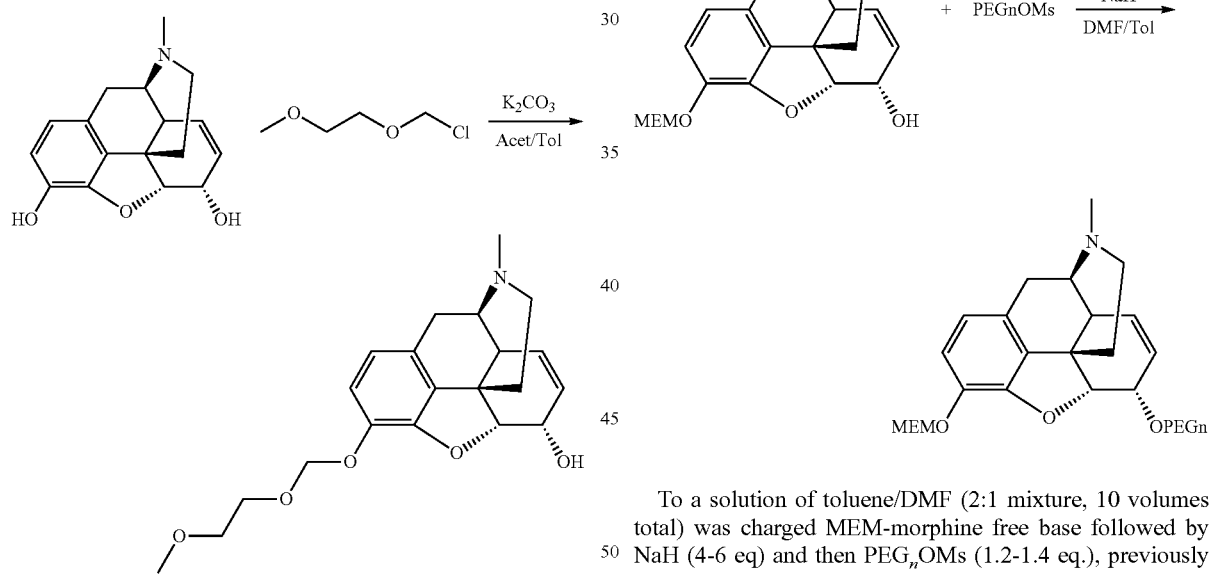

To a suspension of 103 mg of morphine sulfate hydrate (0.26 mmol) in 10 ml of 2:1 acetone:toluene solvent mixture was added 135 mg (1 mmol, 3.7 eq) of K$_2$CO$_3$ and the suspension stirred at room temperature for 25 minutes. To the resulting suspension was added 60 μl (0.52 mmol) of MEMCl and the mixture allowed to react at room temperature. It was sampled after one hour (38% nominal conversion, additional peaks at 1.69 min and 2.28 min), three hours (40% nominal conversion, additional peak at 1.72 min (M+1=493.2)), four and one-half hours (56% nominal conversion, additional peak at 1.73 min), and twenty-three hours (>99% nominal conversion, additional peak at 1.79 min—about 23% of the product peak by height in UV$_{254}$); thereafter, the reaction was quenched with MeOH, evaporated, extracted with EtOAc to give 160 mg of clear oil.

The same reaction was repeated starting with 2 g (5.3 mmol) of morphine sulfate hydrate, 2.2 g (16 mmol, 3 eq) of K$_2$CO$_3$, 1.2 ml (10.5 mmol, 2 eq) of MEMCl in 100 ml of solvent mixture. Sampling occurred after two hours (61% nominal conversion, extra peak at 1.72 min (M+1=492.8)), after one day (80% nominal conversion, extra peak at 1.73 min), after three days (85% nominal conversion, only small impurities, 12 min gradient run), and after six days (91% conversion); thereafter, the reaction was quenched, evaporated, extracted with EtOAc, purified on combi-flash using a 40 g column, DCM:MeOH 0 to 30% mobile phase. Three peaks (instead of two) were identified, wherein the middle peak was collected, 1.15 g (58% yield) of light yellow oil, UV$_{254}$ purity about 87%.

Conjugation of MEM-Protected Morphine to Provide a MEM-Protected Morphine Compound The general approach for conjugating MEM-protected morphine with a water-soluble oligomer to provide a MEM-protected morphine PEG-oligomer compound is schematically shown below.

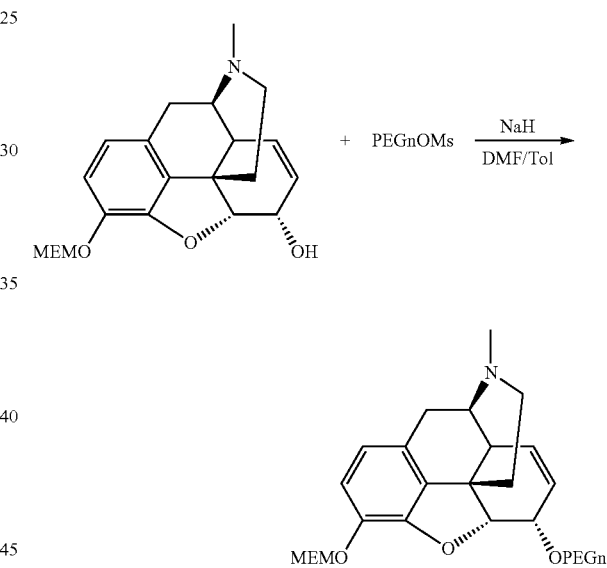

To a solution of toluene/DMF (2:1 mixture, 10 volumes total) was charged MEM-morphine free base followed by NaH (4-6 eq) and then PEG$_n$OMs (1.2-1.4 eq.), previously prepared. The reaction mixture was heated to 55-75° C. and was stirred until reaction completion was confirmed by LC-MS analysis (12-40 hours depending on PEG chain length). The reaction mixture was quenched with methanol (5 volumes) and the reaction mixture was evaporated to dryness in vacuo. The residue was redissolved in methanol (3 volumes) and was chromatographed using a Combiflash system (0-40% MeOH/DCM). The fractions containing large amounts of product were collected, combined and evaporated to dryness. This material was then purified by RP-HPLC to give the products as yellow to orange oils.

Deprotection of MEM-Protected Morphine Compound to Provide a Morphine Compound

The general approach for deprotecting a MEM-protected morphine compound to provide a morphine compound is schematically shown below.

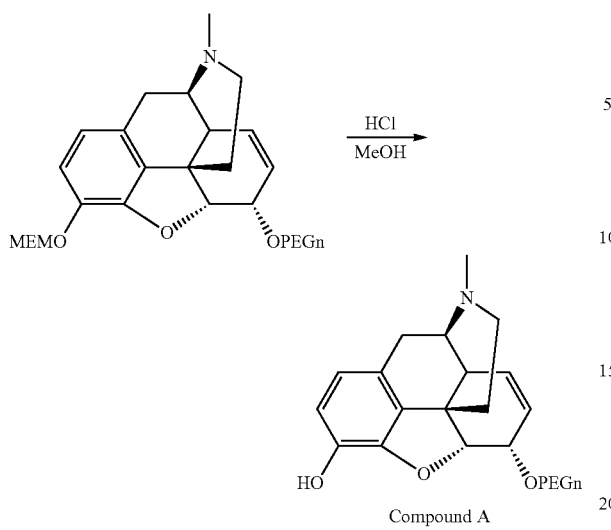

Compound A

To a solution of MEM-protected morphine compound TFA salt suspended in DCM (8 volumes) was charged 6 volumes of 2M HCl in diethyl ether. The reaction mixture was allowed to stir at room temperature for two hours and was then evaporated to dryness under reduced pressure. The oily residue was dissolved in MeOH (8 volumes), filtered through glass wool and then evaporated under reduced pressure to give a thick orange to yellow oil in quantitative yield. Compounds made by this method include: α-6-mPEG$_3$-O-morphine (Compound A, n=3) 217 mg of HCl salt 97% pure (95% by UV254; 98% by ELSD); α-6-mPEG$_4$-O-morphine (Compound A, n=4) 275 mg of HCl salt 98% pure (97% by UV254; 98% by ELSD); α-6-mPEG$_5$-O-morphine (Compound A, n=5) 177 mg of HCl salt 95% pure (93% by UV254; 98% by ELSD); α-6-mPEG$_6$-O-morphine (Compound A, n=6) 310 mg of HCl salt 98% pure (98% by UV254; 99% by ELSD); α-6-mPEG$_7$-O-morphine (Compound A, n=7) 541 mg of HCl salt 96% pure (93% by UV254; 99% by ELSD); and α-6-mPEG-O$_9$-morphine (Compound A, n=9) 466 mg of HCl salt 98% pure (97% by UV254; 99% by ELSD). Additionally, morphine compounds having a single PEG monomer attached, α-6-mPEG$_1$-O-morphine (Compound A, n=1), 124 mg of HCl salt, 97% pure (95% pure by UV$_{254}$; 98% by ELSD); as well as α-6-mPEG$_2$-O-morphine (Compound A, n=2), 485 mg of HCl salt, 97% pure (95% pure by UV$_{254}$; 98% by ELSD) were similarly prepared.

Example 2

Preparation of mPEG$_n$-O-Codeine Compounds

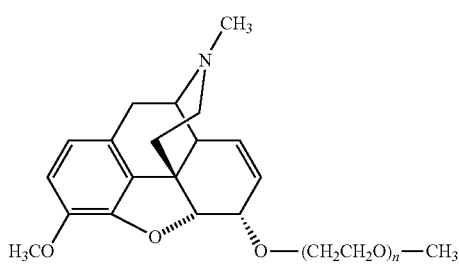

The general approach for conjugating codeine with an activated sulfonate ester of a water-soluble oligomer (using mPEG$_3$OMs as a representative oligomer) to provide a codeine compound is schematically shown below.

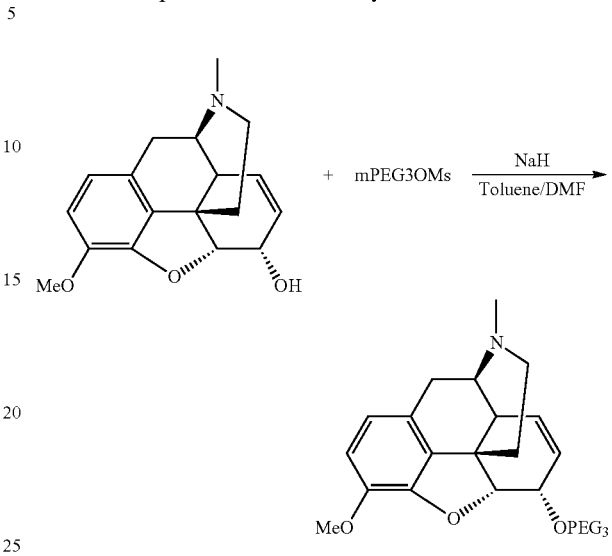

Codeine (30 mg, 0.1 mmol) was dissolved in toluene/DMF (75:1) solvent mixture followed by addition of HO—CH$_2$CH$_2$OCH$_2$CH$_2$OCH$_2$CH$_2$OMs (44 ml, 2 eq) and NaH (60% suspension in mineral oil, 24 mg, 6 eq). The resulting homogeneous yellow solution was heated to 45° C. After one hour, the reaction showed 11% conversion (extra peak at 2.71 min, 12 min run), after eighteen hours, the reaction showed 7% conversion (extra peak at 3.30 min, 12 min run), and after 24 hours, the reaction showed 24% conversion (multitude of extra peaks, two tallest ones are 1.11 min and 2.79 min). At this point, an additional 16 mg of NaH was added and heating continued for six hours, after which, an additional 16 mg of NaH was added followed by continued heating over sixty-six hours. Thereafter, no starting material remained, and analysis revealed many extra peaks, the two tallest ones corresponding to 2.79 min and 3 min (product peak is the second tallest among at least 7 peaks).

This synthesis was repeated using 10× scale wherein 30 ml of solvent mixture was used. After eighteen hours, analysis revealed 71% nominal conversion with additional peaks in the UV (one tall peak at 3.17 min and many small ones; wherein the desired peak corresponded to 3.43 min in UV). Thereafter, 80 mg (2 mmol) of NaH was added followed by continued heating. After three hours, analysis revealed 85% nominal conversion (several extra peaks, main 3.17 min). Reaction mixture was diluted with water, extracted with EtOAc (3×, combined organic layer washed with brine, dried over MgSO$_4$, filtered and rotary evaporated) to give yellow oil (no sm in LC-MS, 90% pure by ELSD, 50% pure by UV-major impurity at 3.2 min). The crude product was dissolved in DCM, applied to a small cartridge filled with 230-400 mesh SiO$_2$, dried, eluted on a Combi-flash via a 4 g pre-packed column cartridge with solvent A=DCM and solvent B=MeOH, gradient 0 to 30% of B. Analysis revealed two peaks of poor symmetry: a small leading peak and a larger peak with a tail. LC-MS was used to analyze fractions, wherein none were identified as containing pure product. Combined fractions that contained any product (tt#22-30) yielded, following solvent evaporation, 150 mg (34% yield) of impure product (LC-MS purity at 3.35 min by UV254, wherein about 25% represented the main impurities 3.11 min, 3.92 min, 4.32 min, 5.61 min of a 12 min run). A second purification by HPLC (solvent A=water, 0.1% TFA; solvent B=acetonitrile, 0.1% TFA) employing a gradient corresponding to 15-60% B, 70 min, 10 ml/min) resulted in poor separation from adjacent peaks. Only two fractions were clean enough and gave 21 mg of TFA salt (>95% pure, 4.7% yield). Three additional fractions both before and after the desired product-containing fractions (for a total of six additional fractions were combined to give 70 mg of about 50% pure product as TFA salts.

Using this same approach, other compounds differing by the number of ethylene oxide units (n=4, 5, 6, 7, and 9) were made using these NaH conditions outlined above.

Conversion of Codeine-Oligomer Compound TFA Salts to Codeine-Oligomer Compound HCl Salts.

The general approach for converting codeine-oligomer TFA salts to codeine-oligomer HCl salts is schematically shown below.

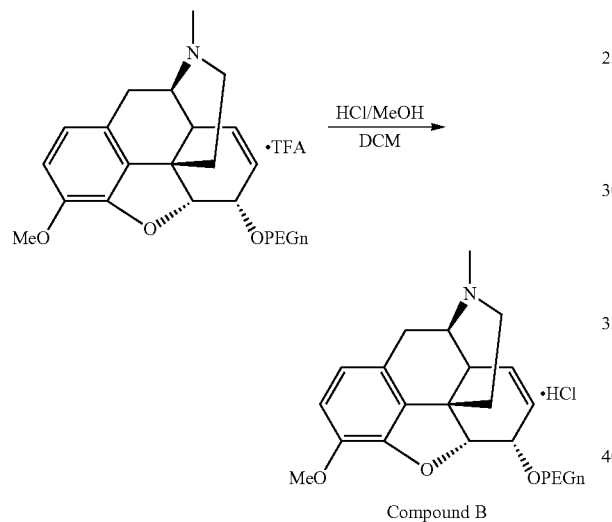

Compound B

To a solution of codeine-oligomer compound TFA salt suspended in DCM (8 volumes) was charged 6 volumes of 2M HCl in diethyl ether. The reaction mixture was allowed to stir at room temperature for two hours and was then evaporated to dryness under reduced pressure. The oily residue was dissolved in MeOH (8 volumes), filtered through glass wool and then evaporated under reduced pressure to give a thick orange to yellow oil in quantitative yield. Following this general procedure, the following compounds were synthesized: α-6-mPEG$_3$-O-codeine (Compound B, n=3) 235 mg of HCl salt, 98% pure; α-6-mPEG$_4$-O-codeine (Compound B, n=4) 524 mg of HCl salt, 98% pure; α-6-mPEG$_5$-O-codeine (Compound B, n=5) 185 mg of HCl salt, 98% pure+119 mg of HCl salt 97% pure, α-6-mPEG$_6$-O-codeine (Compound B, n=6) 214 mg of HCl salt, 97% pure; α-6-mPEG$_7$-O-codeine (Compound B, n=7) 182 mg of HCl salt, 98% pure; α-6-mPEG$_9$-O-codeine (Compound B, n=9) 221 mg of HCl salt, 97% pure; α-6-mPEG$_1$-O-codeine (Compound B, n=1) 63 mg of HCl salt, 90% pure; and α-6-mPEG$_2$-O-codeine (Compound B, n=2) 178 mg of HCl salt, 90% pure.

Example 3

Preparation of mPEG$_n$-O-Hydroxycodone Compounds

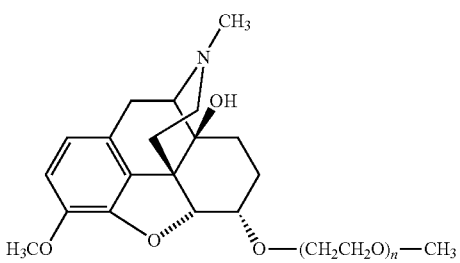

The general approach for conjugating hydroxycodone with an activated sulfonate ester of a water-soluble oligomer (using "mPEG$_n$OMs" as a representative oligomer) to provide a hydroxycodone compound is schematically shown below.

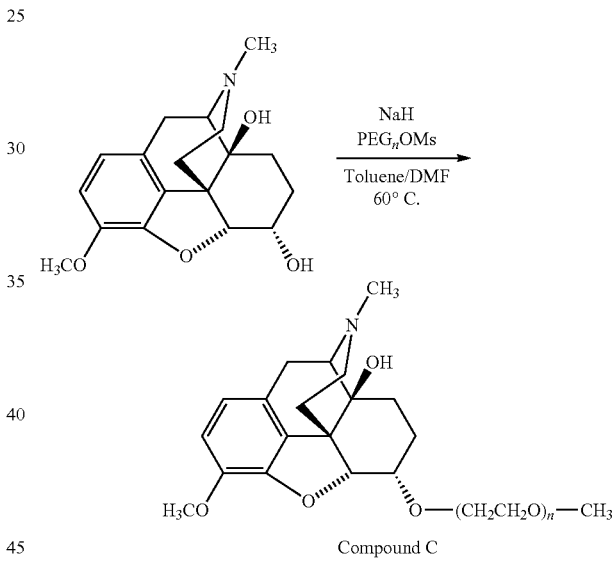

Compound C

Reduction of Oxycodone to α-6-Hydroxycodone:

To a solution of oxycodone free base in dry THF under nitrogen cooled at −20° C., was added a 1.0 M THF solution of potassium tri-sec-butylborohydride over 15 minutes. The solution was stirred at −20° C. under nitrogen for 1.5 hours and then water (10 mL) was added slowly. The reaction mixture was stirred another 10 minutes at −20° C. and then allowed to warm to room temperature. All solvents were removed under reduced pressure and CH$_2$Cl$_2$ was added to the remaining residue. The CH$_2$Cl$_2$ phase was extracted with a 0.1 N HCl/NaCL water solution and the combined 0.1 N HCl solution extracts were washed with CH$_2$Cl$_2$, then Na$_2$CO$_3$ was added to adjust the pH=8. The solution was extracted with CH$_2$CL$_2$. The CH$_2$Cl$_2$ extracts were dried over anhydrous Na$_2$SO$_4$. After removing the solvent under reduced pressure, the desired α-6-HO-3-hydroxycodone was obtained.

Conjugation of mPEG$_n$OMs to α-6-Hydroxycodone:

To a solution of Toluene/DMF (2:1 mixture, 10 volumes total) was charged hydroxycodone (prepared as set forth in the preceding paragraph) followed by NaH (4 eq) and then mPEG$_n$OMs (1.3 e.). The reaction mixture was heated to 60-80° C. and was stirred until reaction completion was confirmed by LC-MS analysis (12-40 hours depending on PEG chain length). The reaction mixture was quenched with methanol (5 volumes) and the reaction mixture was evaporated to dryness in vacuo. The residue was re-dissolved in methanol (3 volumes) and was chromatographed using Combiflash (0-40% MeOH/DCM). The fractions containing large amounts of product were collected, combined and evaporated to dryness. This material was then purified by RP-HPLC to provide the final products as yellow to orange oils.

Conversion of Hydroxycodone Compound TFA Salts to Hydroxycodone Compound HCl Salts To a solution of hydroxycodone compound TFA salt suspended in DCM (8 volumes) was charged 6 volumes of 2M HCl in diethyl ether. The reaction mixture was allowed to stir at room temperature for two hours and was then evaporated to dryness under reduced pressure. The oily residue was dissolved in MeOH (8 volumes), filtered through glass wool and then evaporated under reduced pressure to give a thick orange to yellow oil in quantitative yield. Following this general procedure, the following compounds were synthesized: α-6-mPEG$_3$-O-oxycodone (aka α-6-mPEG$_3$-O-hydroxycodone) (Compound C, n=3) 242 mg of HCl salt, 96% pure; α-6-mPEG$_4$-O-oxycodone (aka α-6-mPEG$_4$-O-hydroxycodone) (Compound C, n=4) 776 mg of HCl salt, 94% pure; α-6-mPEG$_5$-O-oxycodone (aka α-6-mPEG$_5$-O-hydroxycodone) (Compound C, n=5) 172 mg of HCl salt, 93% pure; α-6-mPEG$_6$-O-oxycodone (aka α-6-mPEG$_6$-O-hydroxycodone) (Compound C, n=6) 557 mg of HCl salt, 98% pure; α-6-mPEG$_7$-O-oxycodone (aka α-6-mPEG$_7$-O-hydroxycodone) (Compound C, n=7) 695 mg of HCl salt, 94% pure; and α-6-mPEG$_9$-O-oxycodone (aka α-6-mPEG$_9$-O-hydroxycodone) (Compound C, n=9) 435 mg of HCl salt 95% pure. The following compounds, α-6-mPEG$_1$-O-oxycodone (aka α-6-mPEG$_1$-O-hydroxycodone) (Compound C, n=1) 431 mg of HCl salt 99% pure; and α-6-mPEG$_2$-O-oxycodone (aka α-6-mPEG$_2$-O-hydroxycodone) (Compound C, n=2) 454 mg HCl salt, 98% pure, were similarly prepared.

Example 4

Preparation of Oligomer-Fentanyl Compounds mPEG$_n$-O-fentanyl compounds can be prepared following the approaches schematically shown below. Conventional organic synthetic techniques are used in carrying out the synthetic approaches.

An exemplary approach for preparing the following structures, where the PEG oligomer is positioned, i.e., covalently attached, at the N-(1-(2-phenylethyl)piperidin-4-yl) phenyl group:

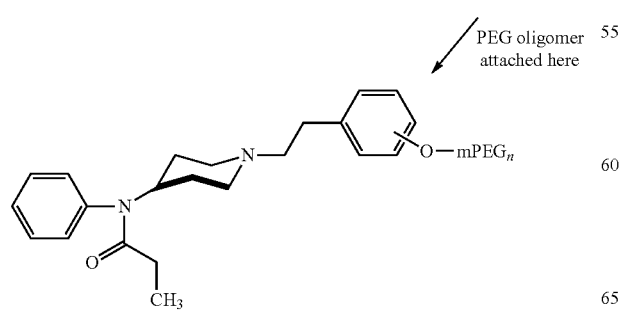

[wherein mPEG$_n$ is —(CH$_2$CH$_2$O)$_n$—CH$_3$ and n is an integer from 1 to 9], is provided below.

Scheme 4-A

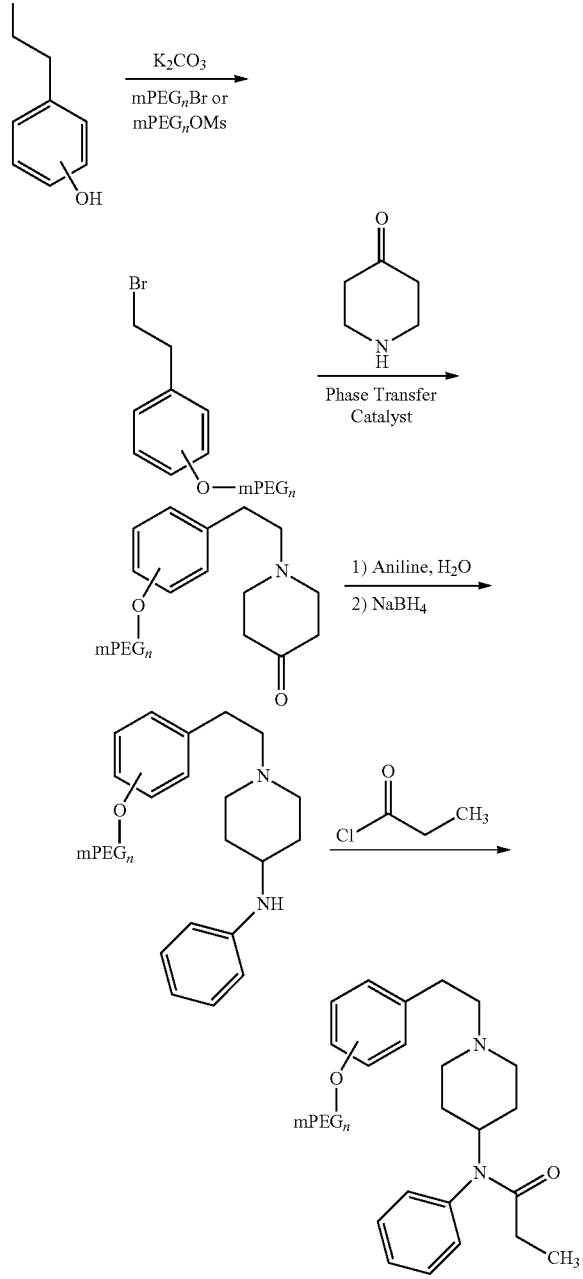

In the above approach, the starting material is a (haloethyl)hydroxybenzene, where the hydroxy group forms the point of attachment for the PEG oligomer. The (haloethyl)hydroxybenzene, i.e., (bromoethyl)hydroxybenzene, is reacted with a mesylated or halogenated activated mPEG oligomer, thereby forming the desired PEG-oligomer modified (haloethyl)benzene intermediate. This intermediate is then reacted with piperidin-4-one in the presence of a phase transfer catalyst; the bromo group reacts at the piperidine-4-one nitrogen to form a next intermediate, 1-(mPEG$_{olig}$-phenylethyl)piperidine-4-one. The ketone functionality is then reduced in the presence of a reducing agent such as sodium borohydride, and converted to an amino group, i.e., N-phenyl-piperidin-4-amine, by reaction with aniline. Finally, the secondary amino group is converted to a tertiary amine by reaction with propionyl chloride to form the desired product as indicated in the scheme above.

The subject mPEG$_n$-O-fentanyl compounds having the PEG oligomer positioned at the N-(1-(2-phenylethyl)piperidin-4-yl) phenyl group were synthesized using a reaction scheme that was slightly modified from Scheme 4-A above as illustrated in Scheme 4-B below:

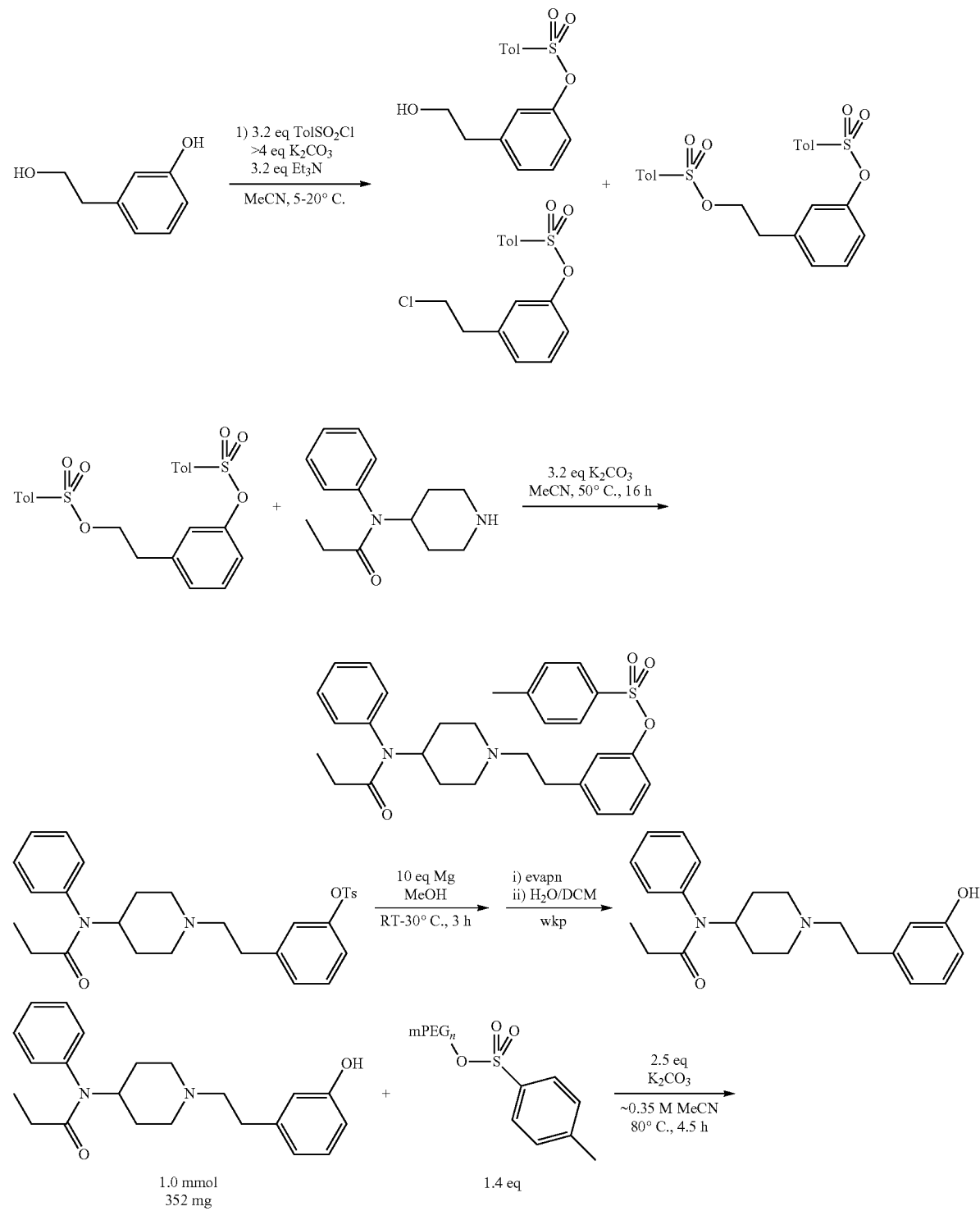

Scheme 4-B

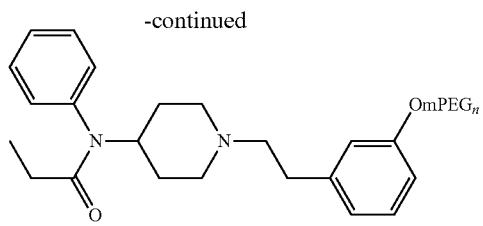

The above approach employs tosyl (p-toluenesulfonate) leaving groups at various steps in the synthesis. The desired PEG-oligomer compounds (n=1 to 9) were assembled by reacting di-tosylated 3-(2-hydroxyethyl)phenol with N-phenyl-N-(piperidin-4-yl)propionamide to form N-(1-(3-hydroxyphenylethyl)piperidin-4-yl)-N-phenylpropionamide, in tosylated form, followed by removal of the tosyl group. The PEG-oligomer group was then introduced into the molecules at the phenyl hydroxyl position by reaction of N-(1-(3-hydroxyphenylethyl)piperidin-4-yl)-N-phenylpropionamide with a molar excess of mPEG$_{olig}$-tosylate to form the desired mPEG$_n$-O-fentanyl compounds. Ratios of reactants and reaction conditions generally employed are provided in the reaction scheme above.

An exemplary approach for providing the following structures, where the PEG oligomer is positioned, i.e., covalently attached, at the N-phenyl group, is set forth below:

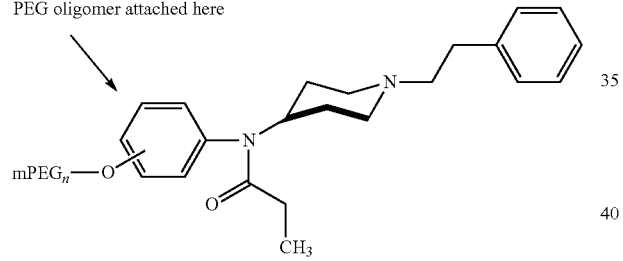

Scheme 4-C

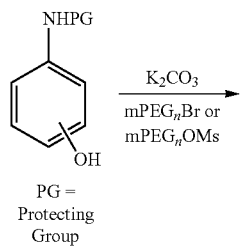

PG = Protecting Group

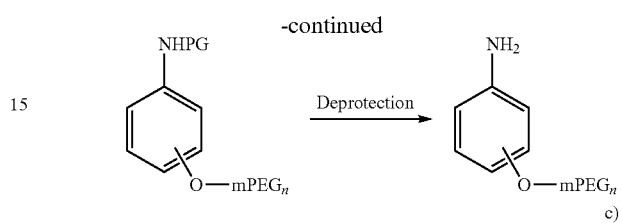

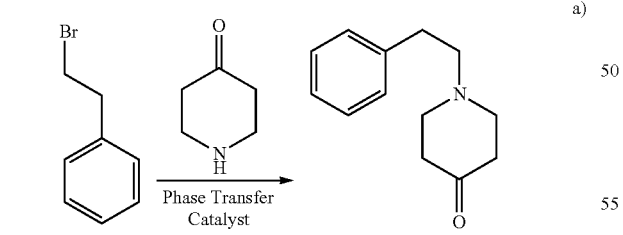

The above exemplary approach for forming an mPEG$_n$-O-fentanyl compound having the PEG oligomer positioned at the N-phenyl ring starts with, e.g., 2-bromoethylbenzene, as the starting material. The 2-bromoethylbenzene is reacted with piperidin-4-one in the presence of a phase transfer catalyst to thereby form the resulting 1-phenethylpiperidin-4-one. The 1-phenethylpiperidin-4-one is coupled to mPEG$_{olig}$-substituted aniline, which is prepared by taking N-protected hydroxyaniline and reacting it with activated mPEG oligomer, such as bromomethoxyPEG$_{olig}$ or mPEG$_{oligo}$ mesylate, followed by removal of the protecting group (see step (b) above). As indicated in reaction step (c) above, 1-phenethylpiperidin-4-one is reacted with mPEG$_{olig}$-substituted aniline in the presence of a reducing agent to convert the keto group into an amine to form the intermediate, 1-phenylethylpiperidin-4-ylamino-mPEG$_{olig}$obenzene. Finally, the secondary amino group is converted to a tertiary amine by reaction with propionyl chloride to form the desired product as indicated in the scheme above.

The subject mPEG$_n$-O'-fentanyl compounds having the PEG oligomer positioned at the N-phenyl group were synthesized using a reaction scheme that was slightly modified from Scheme 4-C above as illustrated in Scheme 4-D below:

Scheme 4-D

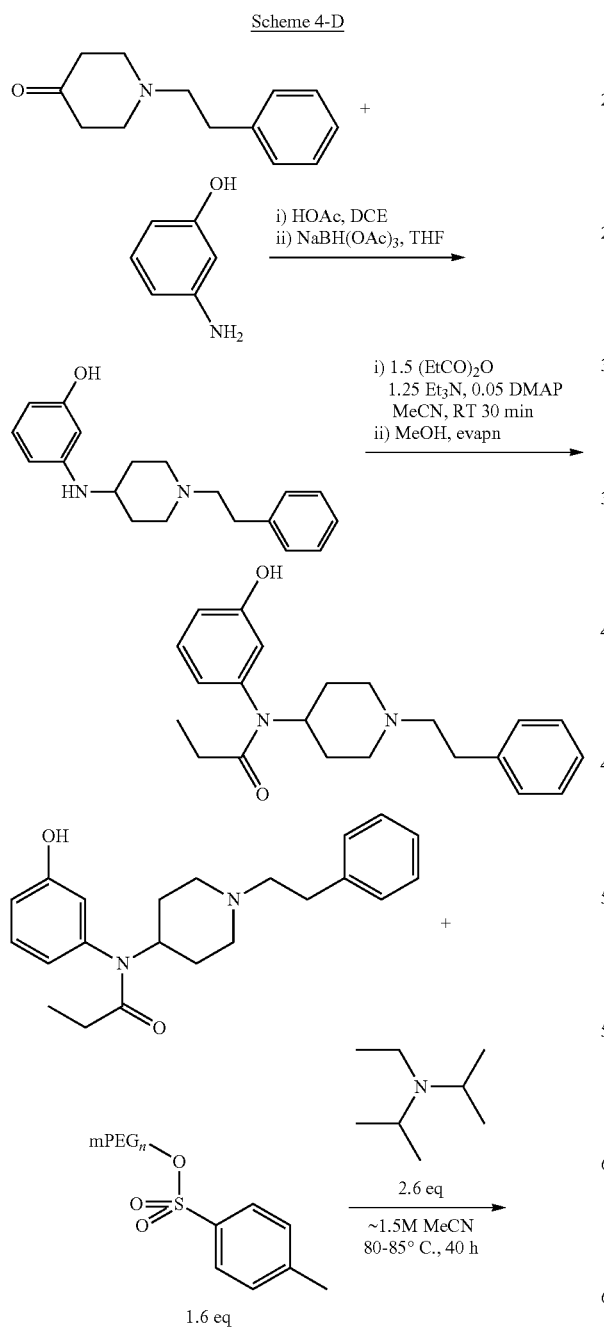

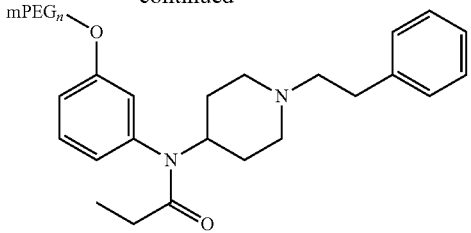

As indicated in Scheme 4-D above, the desired mPEG$_n$-O-fentanyl compounds were prepared by first reacting 1-phenethylpiperidin-4-one with 3-aminophenol under reducing conditions to thereby convert the keto functionality into an amine, i.e., by reaction with the amino group of 3-aminophenol. The product, 3-(1-phenethylpiperidin-4-ylamino)phenol, was then reacted with propionic anhydride in the presence of base (e.g., triethyl amine) and dimethyl-aminopyridine (DMAP) under conditions effective to form N-(3-hydroxyphenyl)-N-(1-phenethylpiperidin-4-yl)propionamide. Finally, introduction of the oligomeric PEG functionality was carried out by reacting the precursor, N-(3-hydroxyphenyl)-N-(1-phenethylpiperidin-4-yl) propionamide, with a molar excess of mPEG$_{oligo}$tosylate under coupling conditions effective to form the desired compounds. Ratios of reactants and reaction conditions generally employed are provided in the reaction schemes above.

Example 4A

Preparation of m-mPEG$_n$-O-Fentanyl Compounds

Synthesis of m-mPEG$_1$-O-Fentanyl Compound (n=1)

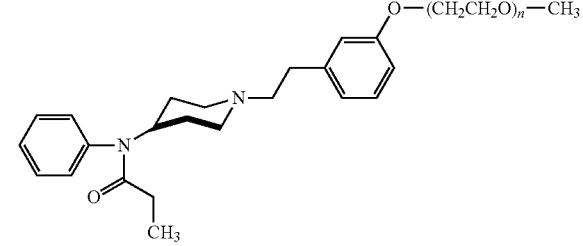

Using an approach set forth in Example 4 and as described schematically in Scheme 4-B, the above compound was prepared.

Synthesis of m-mPEG$_2$-O-Fentanyl Compound (n=2)

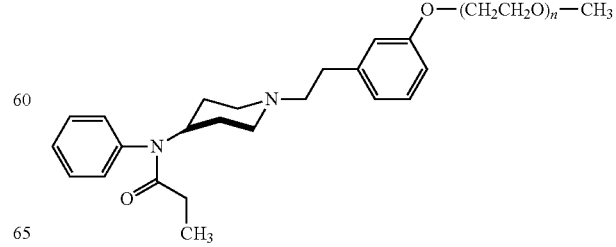

Using an approach set forth in Example 4 and as described schematically in Scheme 4-B, the above compound was prepared.

Synthesis of m-mPEG$_3$-O-Fentanyl Compound
(n=3)

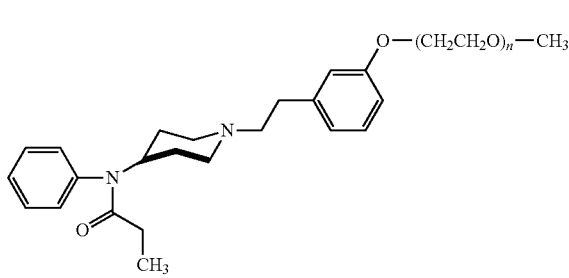

Using an approach set forth in Example 4 and as described schematically in Scheme 4-B, the above compound was prepared.

Synthesis of m-mPEG$_4$-O-Fentanyl Compound
(n=4)

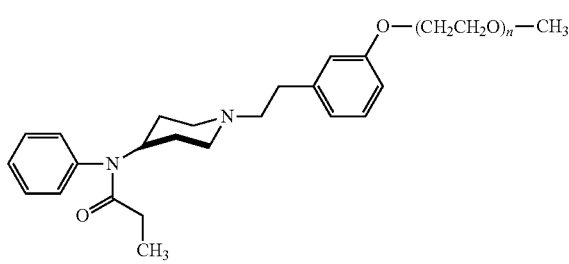

Using an approach set forth in Example 4 and as described schematically in Scheme 4-B, the above compound was prepared.

Synthesis of m-mPEG$_5$-O-Fentanyl Compound
(n=5)

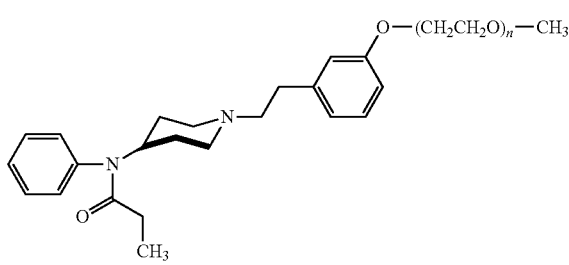

Using an approach set forth in Example 4 and as described schematically in Scheme 4-B, the above compound was prepared.

Synthesis of m-mPEG$_6$-O-Fentanyl Compound
(n=6)

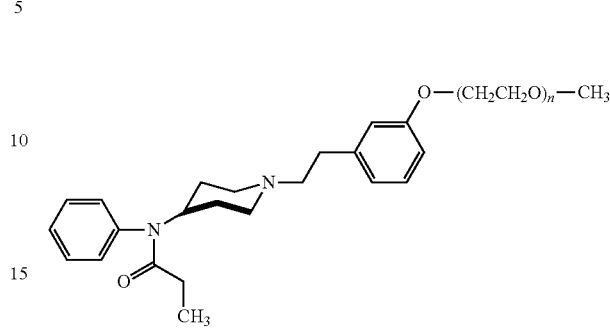

Using an approach set forth in Example 4 and as described schematically in Scheme 4-B, the above compound was prepared.

Synthesis of m-mPEG$_7$-O-Fentanyl Compound
(n=7)

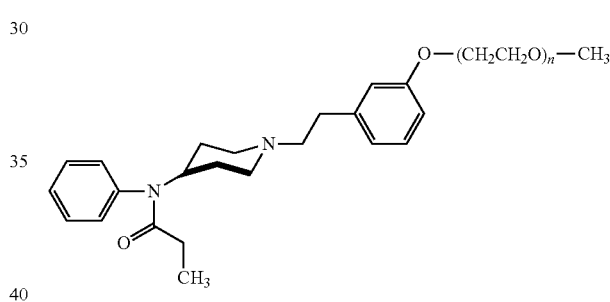

Using an approach set forth in Example 4 and as described schematically in Scheme 4-B, the above compound was prepared.

Synthesis of m-mPEG$_7$-O-Fentanyl Compound
(n=7)

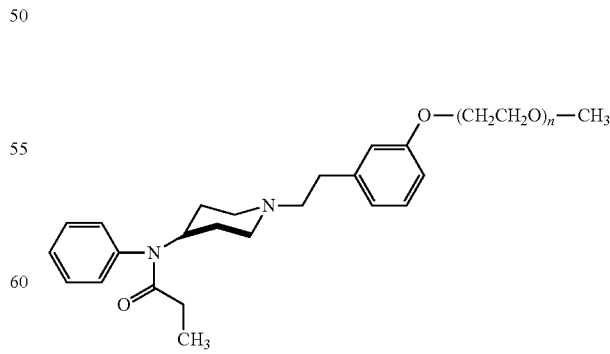

Using a similar approach set forth in Example 4 and as described schematically in Scheme 4-B, the above compound was prepared.

Synthesis of m-mPEG$_8$-O-Fentanyl Compound
(n=8)

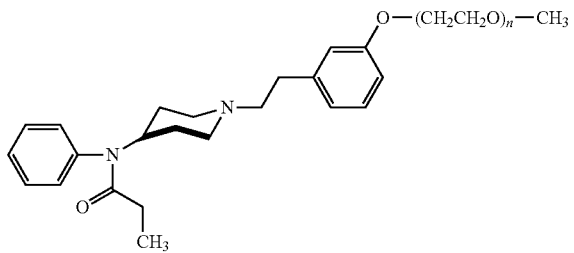

Using an approach set forth in Example 4 and as described schematically in Scheme 4-B, the above compound was prepared.

Synthesis of m-mPEG$_9$-O-Fentanyl Compound
(n=9)

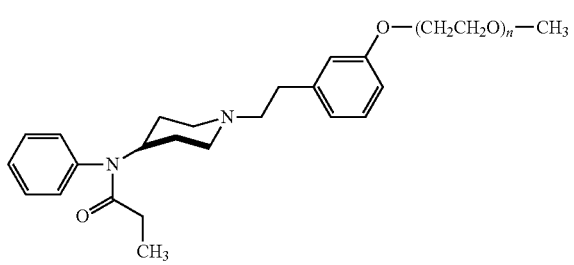

Using an approach set forth in Example 4 and as described schematically in Scheme 4-B, the above compound was prepared.

Each of the above mPEG$_{1-9}$-O-fentanyl compounds was characterized by $^1$H NMR (200 MHz Bruker) and by LC/MS.

Example 5

Preparation of m-mPEG$_n$-O'-Fentanyl Compounds

Synthesis of m-mPEG$_1$-O'-Fentanyl Compound
(n=1)

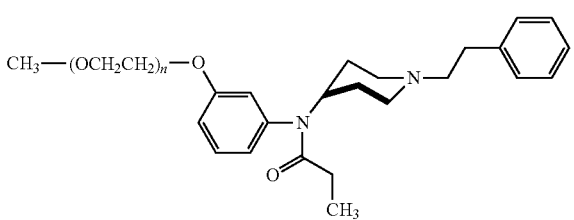

Using an approach set forth in Example 4 and as described schematically in Scheme 4-D, the above compound was prepared. In this series, the oligomeric mPEG was covalently attached at the meta-position of the N-phenyl group

Synthesis of m-mPEG$_2$-O'-Fentanyl Compound
(n=2)

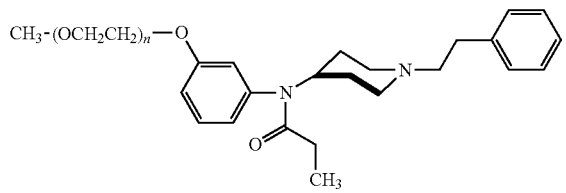

The above compound was prepared using the approach set forth in Example 4 and as described schematically in Scheme 4-D.

Synthesis of m-mPEG$_3$-O'-Fentanyl Compound
(n=3)

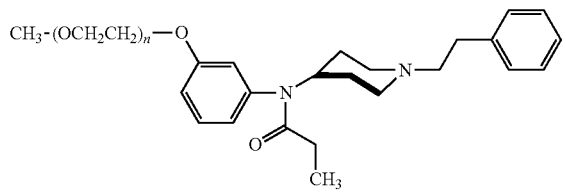

The above compound was prepared using the approach set forth in Example 4 and as described schematically in Scheme 4-D.

Synthesis of m-mPEG$_4$-O'-Fentanyl Compound
(n=4)

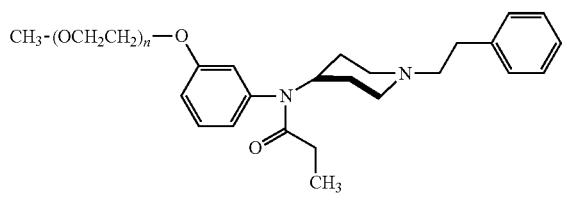

The above compound was prepared using the approach set forth in Example 4 and as described schematically in Scheme 4-D.

Synthesis of m-mPEG$_5$-O'-Fentanyl Compound
(n=5)

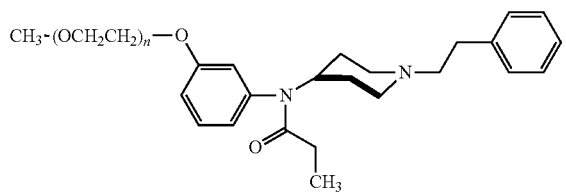

Synthesis of m-mPEG$_6$-O'-Fentanyl Compound
(n=6)

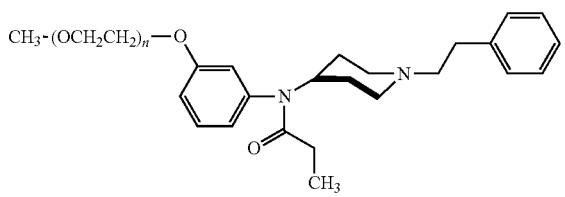

The above compound was prepared using the approach set forth in Example 4 and as described schematically in Scheme 4-D.

Synthesis of m-mPEG$_7$-O'-Fentanyl Compound
(n=7)

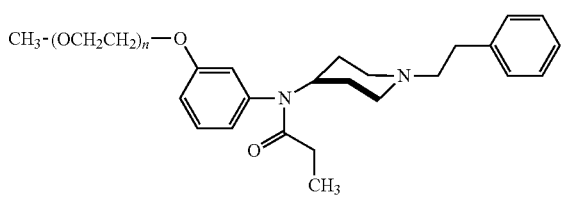

The above compound was prepared using the approach set forth in Example 4 and as described schematically in Scheme 4-D.

Synthesis of m-mPEG$_8$-O'-Fentanyl Compound
(n=8)

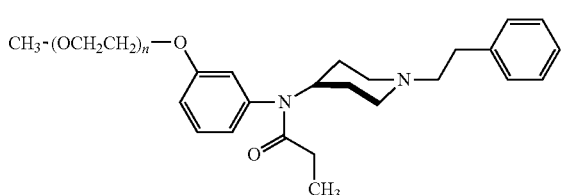

The above compound was prepared using the approach set forth in Example 4 and as described schematically in Scheme 4-D.

Synthesis of m-mPEG$_8$-O'-Fentanyl Compound
(n=8)

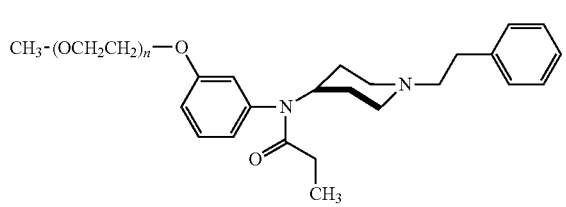

The above compound was prepared using the approach set forth in Example 4 and as described schematically in Scheme 4-D.

Synthesis of m-mPEG$_9$-O'-Fentanyl Compound
(n=9)

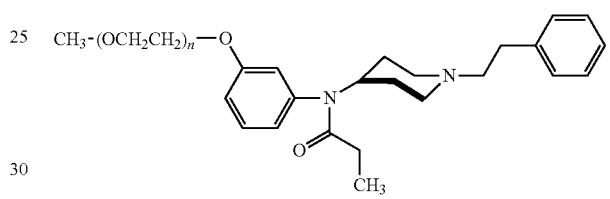

The above compound was prepared using the approach set forth in Example 11 and as described schematically in Scheme 4-D.

Each of the above mPEG$_{1-9}$-O'-fentanyl compounds were characterized by $^1$H NMR (200 MHz Bruker) and by LC/MS.

Example 6

Preparation of para-mPEG$_n$-O'-Fentanyl Compounds

Synthesis of p-mPEG$_1$-O'-Fentanyl Compound
(n=1)

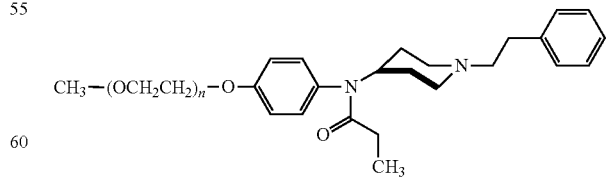

The above compound can be prepared using an approach set forth in Example 4. In this series, the oligomeric mPEG is covalently attached at the para-position of the N-phenyl group.

Synthesis of p-mPEG$_4$-O'-Fentanyl Compound
(n=4)

The para-substituted compound was prepared according to the reaction scheme shown below:

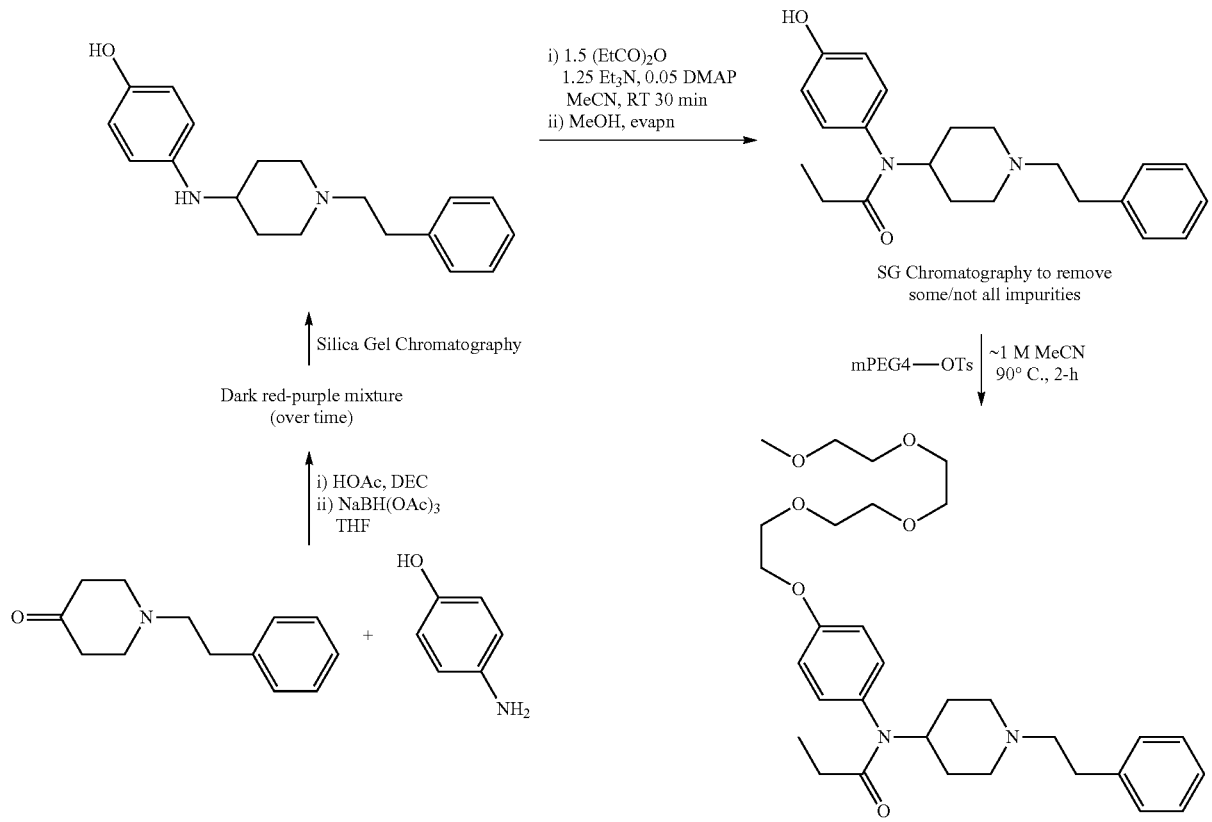

The desired pPEG$_4$-O-fentanyl compound was prepared by first reacting 1-phenethylpiperidin-4-one with 4-aminophenol under reducing conditions (e.g., in the presence of a reducing agent such as NaBH(OAc)$_3$) to thereby convert the keto functionality into an amine, i.e., by reaction with the amino group of 4-aminophenol. The product, 4-(1-phenethylpiperidin-4-ylamino)phenol, was then reacted with propionic anhydride in the presence of base (e.g., triethyl amine) and dimethylaminopyridine (DMAP) under conditions effective to form N-(4-hydroxyphenyl)-N-(1-phenethylpiperidin-4-yl)propionamide. Finally, introduction of the oligomeric PEG functionality was carried out by reacting the precursor, N-(4-hydroxyphenyl)-N-(1-phenethylpiperidin-4-yl)propionamide, with a mPEG$_4$tosylate under coupling conditions effective to form the desired compound. Ratios of reactants and reaction conditions generally employed are provided in the reaction scheme above.

Additional pPEG$_{oligo}$-O-fentanyl compounds may be similarly prepared.

Example 7

In Vivo Analgesis Assay: Acetic Acid Writhing in Mice

The analgesic potency of certain oligomeric PEG-opioid compounds, mPEG$_n$-O-hydroxycodone (e.g. α-6-mPEG$_n$-O-hydroxycodone, See Example 3), in combination with diclofenac were determined using an acetic acid writhing assay in mice.

Mice were given a single dose of control solution or two separate oral doses (larger volume immediately after administration of a smaller volume) of a PEG-opioid agonist compound (α-6-mPEG$_n$-O-hydroxycodone (n=4, 5, 6)) and diclofenac 30 minutes prior to intraperitoneal administration of 0.5% acetic acid (0.1 mL/10 g bodyweight). Acetic acid induces "writhing" which includes: contractions of the abdomen, twisting and turning of the trunk, arching of the back and the extension of the hindlimbs. After the injection the animals were placed in an observation beaker and their behavior was observed. Contractions were counted in four, five minute segments, between 0 and 20 minutes after the acetic acid injection. The animals were used once and euthanized immediately following the completion of the study. Each compound was tested at dose range of 1-100 mg/kg.

Table 1 provides a summary the acetic acid writhing mean total number of writhes for the tested compounds in combination with Diclofenac (3 mg/kg).

TABLE 1

| Dose (mg/kg) | Mean Number of writhes | | |
|---|---|---|---|
| | α-6-mPEG$_4$-O-hydroxycodone | α-6-mPEG$_5$-O-hydroxycodone | α-6-mPEG$_6$-O-hydroxycodone |
| 5 | 13 | 7.2 | 6.2 |
| 10 | 4.8 | 1.4 | 4 |

Figure 2:
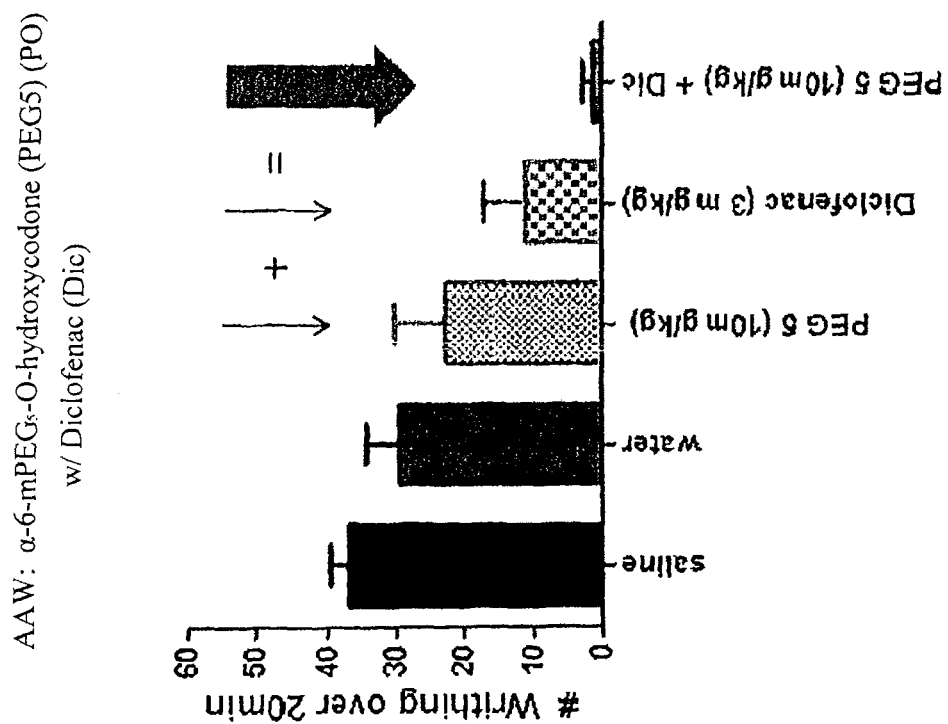
FIG. 2 depicts the results of the acetic acid writhing assay for a combination of certain opioid agonist compounds and analgesics as described in Example 7.

FIG. 1 shows the dose response graphs from the acetic acid writing assay for α-6-mPEG$_n$-O-hydroxycodone (n=5) and diclofenac, administered separately, respectively. FIG. 2 shows the results of the acetic acid writhing assay for a combination of mPEG$_n$-hydroxycodone (α-6-mPEG$_n$-O-hydroxycodone) (n=5) and diclofenac (3 mg/kg). As seen in FIG. 2, the combination of mPEG$_n$hydroxycodone (α-6-mPEG$_n$-O-hydroxycodone) (n=5) and diclofenac results in a measured reduction of writhings that is greater than the number of writhings when each compound is individually administered.

Prophetic Example 8

In-Vivo Analgesic Assay: Hot Plate Latency Assay

The hot plate latency assay may be used as a measure of in vivo bioactivity of the compositions and combinations disclosed herein. This experiment uses a standard hotplate withdrawal assay in which latency of withdrawal from a heat stimulus is measured following administration of a test compound. Compounds are administered to the animal and 30 minutes later, a thermal stimulus is provided to the hindpaw. Latency for hindpaw withdrawal in the presence of morphine is used as the measure of full analgesia, while latency in the presence of saline is used as a negative control for no analgesia. The agonist effect of the test compound is evaluated by measuring time to withdrawal compared with a negative control (saline).

Prophetic Example 9

Evaluation of Opioid Agonist Compounds and NSAIDS in a Rat Model of Inflammation The effects of NSAIDS and PEG-opioid agonist compounds alone and as combination are evaluated in a rat model of inflammatory pain. An injection of 50% Complete Freund's adjuvant (CFA) is injected intra-plantar into the hind paw of rats to induce inflammation. Two days later, test compounds are administered orally to rats within a range of specified doses. CFA evoked mechanical hyperalgesia is measured at baseline and at various times following treatment with test compounds using a paw pressure test (Randall Sellito). CFA causes significant decrease in the paw withdrawal thresholds (baseline) and doses of test compounds or combinations that produce a significant increase in the paw withdrawal threshold from baseline are considered to be efficacious in this model.

What is claimed is:

1. A composition comprising:
   a non-steroidal anti-inflammatory drug (NSAID); and
   an opioid agonist compound of formula:

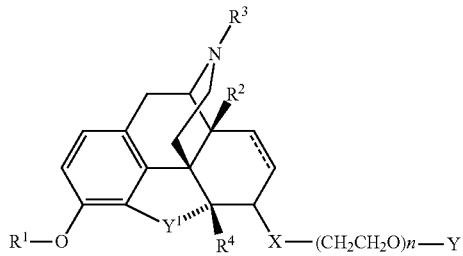

and pharmaceutically acceptable salts thereof, wherein:
   $R^1$ is hydrogen or methyl;
   $R^2$ is hydrogen or hydroxyl;
   $R^3$ is hydrogen, methyl, or cyclobutylmethyl;
   $R^4$ is hydrogen;
   "_____" represents an optional double bond;
   $Y^1$ is O;
   X is a physiologically stable linker;
   n is an integer from 1 to 10; and
   Y is lower alkyl.

2. The composition of claim 1, wherein the opioid agonist compound is:

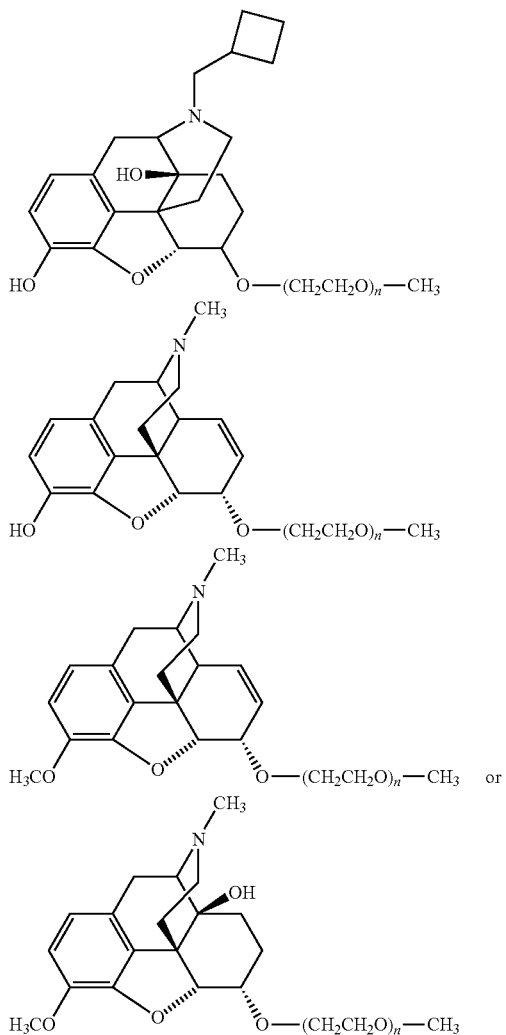

and pharmaceutically acceptable salts thereof.

3. The composition of claim 1, wherein the opioid agonist compound is of the formula:

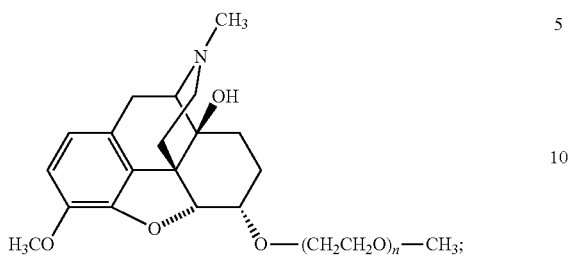

wherein n is an integer selected from 2 to 10; and pharmaceutically acceptable salts thereof.

4. The composition of claim 1, wherein the non-steroidal anti-inflammatory drug (NSAID) is ketorolac, ibuprofen, oxaprozin, indomethecin, etodolac, meloxicam, sulindac, diclofenac, flufenamic acid, difunisal, naproxen, flurbiprofen, ketoprofen, fenoprofen, or acetaminophen.

5. The composition of claim 1 in a unit dosage form.

6. The composition of claim 1, wherein a non-steroidal anti-inflammatory drug (NSAID) is present in the composition.

7. The composition of claim 1, further comprising at least one pharmaceutically acceptable excipient.

8. A method of treating pain in a patient, comprising administering a composition of claim 1 to a patient in need thereof.

* * * * *

UNITED STATES PATENT AND TRADEMARK OFFICE
CERTIFICATE OF CORRECTION

PATENT NO. : 9,457,024 B2  
APPLICATION NO. : 14/356486  
DATED : October 4, 2016  
INVENTOR(S) : Timothy A. Riley et al.

It is certified that error appears in the above-identified patent and that said Letters Patent is hereby corrected as shown below:

In the Claims

In Column 70, Claim 1, Line 20 ""—" represents an optional double bond" should be changed to --"---" represents an optional double bond--.

In Column 71, Claim 6, Line 24 insert --single-- between "a" and "non-steroidal".

Signed and Sealed this
Eleventh Day of April, 2017

Michelle K. Lee
*Director of the United States Patent and Trademark Office*